(12) United States Patent
Augustine et al.

(10) Patent No.: US 10,569,054 B2
(45) Date of Patent: Feb. 25, 2020

(54) CATHETER ANCHORING DEVICE

(71) Applicant: Augustine Biomedical and Design, LLC, Eden Prairie, MN (US)

(72) Inventors: Scott D. Augustine, Deephaven, MN (US); Randall C. Arnold, Minnetonka, MN (US)

(73) Assignee: Augustine Biomedical and Design LLC, Eden Prairie, MN (US)

( * ) Notice: Subject to any disclaimer, the term of this patent is extended or adjusted under 35 U.S.C. 154(b) by 0 days.

(21) Appl. No.: 14/950,502

(22) Filed: Nov. 24, 2015

(65) Prior Publication Data

US 2017/0143941 A1 May 25, 2017

(51) Int. Cl.
*A61M 25/02* (2006.01)
(52) U.S. Cl.
CPC ....... *A61M 25/02* (2013.01); *A61M 2025/024* (2013.01); *A61M 2025/028* (2013.01); *A61M 2025/0253* (2013.01)
(58) Field of Classification Search
CPC ............ A61M 25/02; A61M 2025/024; A61M 2025/0253; A61M 2025/028
See application file for complete search history.

(56) References Cited

U.S. PATENT DOCUMENTS

| 4,633,863 | A | 1/1987 | Filips et al. | |
|---|---|---|---|---|
| 6,827,707 | B2 * | 12/2004 | Wright | A61M 25/02 604/174 |
| 2009/0149814 | A1 * | 6/2009 | Bailey | A61M 25/02 604/180 |
| 2009/0182283 | A1 | 7/2009 | Sloan | |
| 2012/0197204 | A1 | 8/2012 | Helm, Jr. | |

FOREIGN PATENT DOCUMENTS

EP 2328648 B1 6/2011

OTHER PUBLICATIONS

International Search Report and Written Opinion for PCT/US2016/063328, 18 pages; dated Mar. 3, 2017.

* cited by examiner

*Primary Examiner* — Imani N Hayman
(74) *Attorney, Agent, or Firm* — Fredrikson & Byron, P.A.

(57) ABSTRACT

Embodiments include a catheter anchoring device for securing a percutaneous medical catheter inserted at a skin puncture site to a skin of a body. The catheter anchoring device may include a catheter capture portion coupled to a skin attachment portion. The catheter capture portion may be configured to engage with a portion of the catheter protruding from the skin when the catheter is subcutaneously placed in a body. The skin attachment portion may be configured to adhesively attach the anchoring device to the skin, wherein the skin attachment portion is primarily attached to the skin overlaying and lateral to the subcutaneously located catheter.

24 Claims, 22 Drawing Sheets

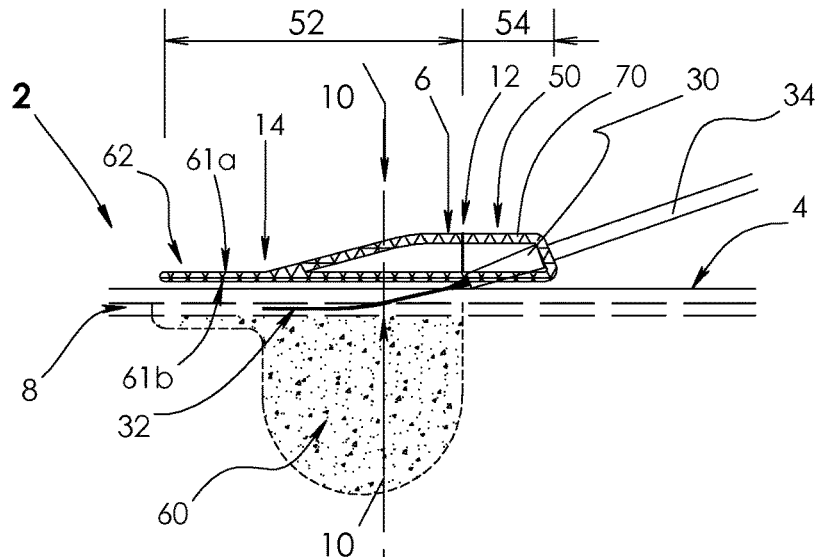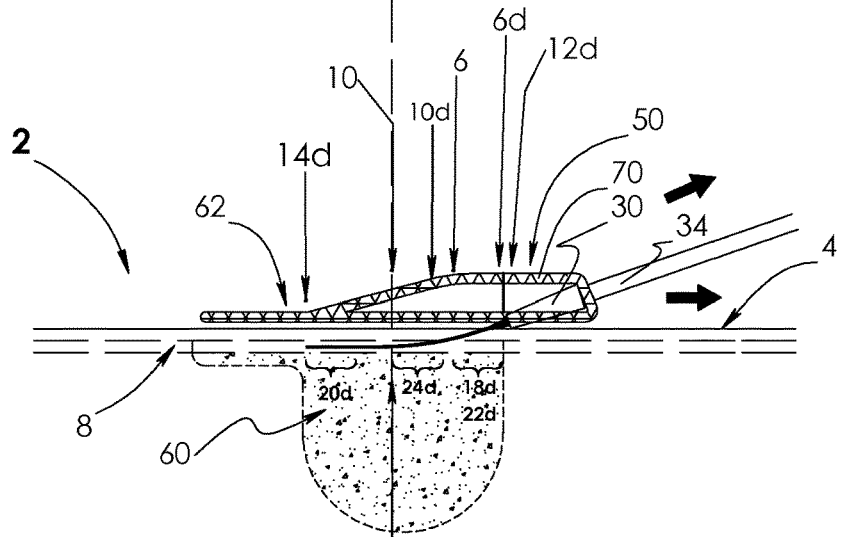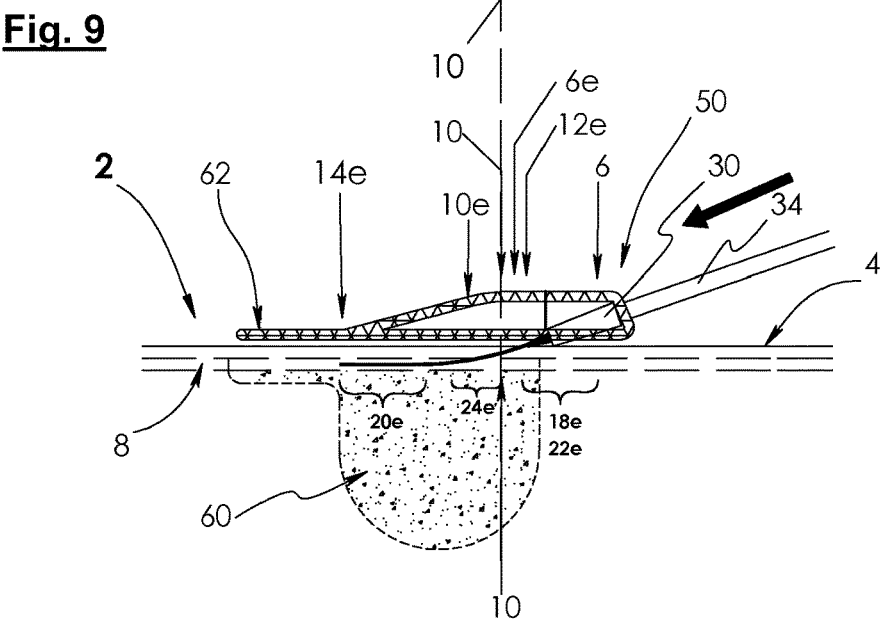

CATHETER ANCHORING DEVICE

BACKGROUND

Plastic catheters have been used for access to veins, arteries, the epidural space and other neural sheath spaces for decades. The catheters are typically introduced through the skin ("percutaneous") either over the outside or within a needle. Alternately they may be introduced over a guide wire that was introduced through the skin inside of a needle. The objective for all medical catheters is to enter a specific space (vein, artery, epidural space, dural space or neural space) and to lie in that space so that fluids or pharmaceuticals that flow from the distal tip of the catheter are delivered to the specific space. The most common of these are IV catheters delivering intravenous fluids and pharmaceuticals into the venous blood.

All percutaneous catheters enter the body through the skin at a puncture site. A catheter then traverses through the subcutaneous tissue for a distance (typically 0.25 to 0.5 the length of the catheter) before entering a vein or artery. The same needle that pierced the skin then pierces the vein or artery and the plastic catheter is advanced off of the needle and into the vein or artery until the catheter hub connector abuts the skin. For example, IV catheters of 1.25 inches or less will typically end up with less than half of the catheter in the vein when the insertion is complete. Therefore, if a catheter is inadvertently pulled even a short distance out of the skin, or if the skin anchoring the catheter is moved relative to the vein, it could result in the tip of the catheter "popping" out of the vein and "blowing" the IV.

When an IV or arterial catheter is fully and properly inserted, the catheter is not visible and the only portion left showing outside the skin is the hub and the tubing connected to the hub. Not surprisingly, since the hub is the only part of the catheter that is accessible, clinicians have used various taping methods to secure the exposed hub and the tubing to the skin adjacent or lateral to the hub, in order to secure the device. In addition, hundreds of catheter-anchoring devices have been described in patents and patent applications. To the instant inventors knowledge, every single one of the prior art catheter anchoring devices secures the hub or tubing, to the skin adjacent the hub.

The fact that catheters are secured to the skin adjacent the hub is the genesis of several problems well-known to plague IV and arterial catheters. The skin is a very stretchy and movable organ. When tension is applied to the skin, it stretches and moves somewhat independently from the skin nearby. Additionally, it also easily moves relative to the underlying skeletal structures such as muscle and bone, because of the loose connective tissue layer that connects the two together. Most of the veins used for IV access lie within this loose connective tissue layer and are thus loosely connected to the skin and also loosely connected to the underlying skeletal structures. When the overlaying skin stretches and moves, it causes the loosely connected adjacent veins to also move. The skin adjacent to the hub is not overlaying and therefore not connected to the portion of the vein that includes the vein puncture site and the catheter tip. Therefore, the vein puncture site and the vein wall adjacent the catheter tip do not move when the skin adjacent the hub is stretched or pulled as occurs with the prior art catheter securing techniques. Many people, especially the elderly, have excess or loose skin which makes this problem even worse.

When the catheter hub that is anchored to the skin adjacent the hub (as in the prior art) is pulled or if the skin adjacent the hub is pulled, the skin can stretch, easily allowing a 0.25 inch movement of the catheter out of the skin puncture site. This also results in a 0.25 inch movement or more of the catheter relative to the vein puncture site which is not under-laying the skin attached to the hub. The first 0.25 inches of movement is due to the skin stretching and laxity between the hub and the skin. An equal or greater movement is caused by the movement of the skin adjacent the hub relative to the vein that is 1-2 inches away from the hub and connected only by loose connective tissue. A total catheter movement of 0.5-0.75 inches may occur at the vein puncture site. IV catheters are also frequently placed near the wrist, where flexion of the wrist creates a movement of the skin that is very similar to the stretching of the skin.

Catheters can also be pulled out by twisting the hub about a vertical access rising perpendicularly from the skin. The twisting action can be caused by an inadvertent lateral pull on the IV tubing. The twisting action can "lever" the catheter out of the skin without stretching the skin.

It is apparent that in the normal course of having an IV with the prior art securing methods, the catheter will be pulled 0.25 inches out of the skin and 0.25-0.75 inches out of the vein many times each day. It then usually slides back into the skin and vein without apparent incident. This catheter movement in and out of the skin can be referred to as "pistoning." However, the negative consequences of the pistoning of the catheter in-and-out of the skin and vein caused by securing the catheter hub to the skin adjacent the hub are significant and relatively frequent:

1. When the catheter is pulled partially out and the vein or artery does not move equally in the same direction, the tip may pop out of the vein or artery puncture site, causing a "blown" or unusable IV or arterial line.

2. Pistoning can result in the relatively stiff tip of the catheter repeatedly poking the wall of the relatively fragile vein until it pokes through the wall and "blows" the IV.

3. When the sterile catheter pulls out of the skin by 0.25 inches or more, it is instantly exposed to a variety of skin bacteria incubating in the warm blood and serum that has oozed from the IV puncture site and is captured by the occlusive dressing that is frequently applied to the IV site. When the catheter is then reintroduced back through the skin, these bacteria which are now coating the catheter, are transported through the skin and deposited into the subcutaneous tissue where they can cause a "line infection."

4. The 0.25-0.75 inch pistoning of the relatively sharp catheter tip against the fragile wall of the vein or artery can abrade the endothelial layer from the vein or arterial wall. This exposes the deeper structures of the vein or artery to the blood. These deeper structures are well known to be thrombogenic, meaning that the injured but not perforated vein or artery may cause a blood clot to form within the vessel.

5. Twisting of the hub relative to the catheter not only causes pistoning of the catheter but also may kink the catheter, preventing fluid flow.

Central venous catheters, epidural catheters and neural block catheters are typically much longer than IV or arterial catheters. Central venous catheters typically do not pop out of the vein or "blow" by poking out of the vein, however, they may kink occluding flow or piston in-and-out increasing the probability of line infections. Epidural and neural sheath catheters can pull out and become dislodged from the proximity of the nerve and thus become non-functional. These catheters are also easily kinked and thus occluded.

Blown IVs, kinked IVs, line infections and venous or arterial thrombosis are all well-known complications of venous and arterial catheters. Dislodgement or kinking of epidural and neural catheters are also well known problems. Clearly there is a need for a better catheter anchoring device that prevents these well-known problems associated with prior art catheter securing devices and adhesive tape techniques for anchoring medical catheters.

SUMMARY

In general, this disclosure is directed to catheter anchoring devices and methods.

This invention is a catheter anchoring device comprising two components. The first is a skin attachment portion that adhesively attaches the anchoring device to the skin. The second is a catheter capture portion that engages with the catheter or hub of the catheter that is protruding from the skin after percutaneous placement of the catheter into a body.

The fundamental difference between the instant invention and all other catheter anchoring devices and techniques known to the instant inventors, is that the skin attachment portion of this invention is primarily attached to the skin overlaying and lateral to the subcutaneously located catheter. This is in sharp contrast to the prior art devices that attach to the skin adjacent the hub of the catheter. Therefore, this invention primarily attaches to the skin that is on the opposite side of the skin puncture site, compared to the prior art.

It will be apparent that attaching to the skin over the subcutaneously located catheter is fundamentally advantageous compared to attaching to the skin adjacent to the hub on the opposite side to the skin puncture site. First, if the IV line, catheter hub or skin attachment portion is pulled, the resulting movement of the skin at the attachment site moves the adjacent skin puncture site simultaneously in the same direction as the catheter movement. This results in no net movement between the puncture site and the catheter and thus the catheter is not pulled out of the skin by a longitudinal movement of the attachment portion or the skin that it is attached to.

In addition, the vein puncture site and the portion of the vein adjacent to the tip of the catheter, lie under the skin that is adhesively attached to the skin attachment portion of the instant invention. The skin overlaying the vein is connected to the vein by loose connective tissue. The portion of the vein containing the catheter will correspondingly move simultaneously in the same direction as the moving overlaying skin. Therefore, inadvertent longitudinal movement of the catheter and skin attachment portion of the instant invention, results in a corresponding movement of the attached skin and corresponding movement of the under-laying vein that is attached to the moving skin in the same direction as the moving skin.

The fact that the catheter, the skin attachment portion of this invention, the skin attached to the skin attachment portion including the immediately adjacent skin puncture site, and the under-laying vein containing the catheter, all correspondingly move simultaneously in the same direction with any movement of the catheter, is critical to understanding this invention. Since the catheter and the skin puncture site move together, there is no net movement between them and a movement of the catheter does not result in the catheter being pulled out of the skin, in contrast to the prior art. Since the catheter and the vein puncture site move together, there is minimal net movement between them and a movement of the catheter does not result in the catheter being pulled out of the vein, in contrast to the prior art. Since the catheter and the wall of the vein adjacent the catheter tip move together, there is minimal net movement between them and a movement of the catheter does not result in the catheter being poked through the fragile wall of the vein or abrading the wall of the vein, in contrast to the prior art.

The axis for twisting this invention naturally lies at a center point of the skin attachment portion, which is located over the subcutaneous catheter. However, the hub of the catheter is located on the opposite side of the skin puncture site and therefore cannot be twisted about an axis because it does not have a natural axis formed by an attachment to the skin at that location. The fact that the skin attachment site is a distance from the hub creates a "lever" that prevents twisting of the hub. The secure anchor design of the instant invention virtually eliminates the possibility of twisting the hub about an axis and kinking the catheter.

Some prior art catheter anchoring devices and adhesive tape catheter anchoring techniques may include relatively large pieces of plastic film overlaying the skin puncture site and the surrounding skin. It may not be obvious where the structural adhesive attachment that physically secures the catheter hub to the patient occurs. This can be easily determined by twisting the catheter hub. If the skin adjacent the hub moves in a twisting motion as a result of twisting the hub, the catheter anchoring device or technique is attached primarily to the skin adjacent the hub and is thus consistent with the prior art. If the skin overlaying the subcutaneous catheter moves in a twisting motion as a result of twisting the hub, the catheter anchoring device or technique is attached primarily to the skin overlaying the subcutaneous catheter and is thus consistent with the instant invention. Alternately, the skin attachment location can be determined by a lateral movement of the catheter hub. If the skin overlaying the subcutaneous catheter moves in a lateral motion as a result of a lateral movement the hub, the catheter anchoring device or technique is attached primarily to the skin overlaying the subcutaneous catheter and is thus consistent with the instant invention.

The basic design of the invention described herein captures the hub of the IV, arterial or some central venous catheters. It must be understood that minor variations of this design are anticipated and will effectively capture the tubing itself in the case of some central venous catheters, epidural catheters and neural sheath catheters.

A small heat pack, for example utilizing an iron oxidation reaction or other chemical reaction, maybe attached to the catheter anchoring device of the instant invention. Since catheters are introduced through the skin and the skin is usually significantly hypothermic, it is advantageous to warm the skin at the catheter site to normothermia (normal temperature). Normothermia or even mild hyperthermia, is well known to activate the immune system at the wound in the skin, to promote blood flow through the vein and to minimize the chance of thrombosis in the vein.

The details of one or more examples are set forth in the accompanying drawings and the description below. Other features, objects, and advantages will be apparent from the description and drawings, and from the claims.

BRIEF DESCRIPTION OF DRAWINGS

FIG. 7 is a side view of the illustrative catheter anchoring device of FIG. 5 as applied to a cross-section of the patient (e.g., an arm).

FIG. 8 is a side view of the illustrative catheter anchoring device as applied to the cross-section of the patient of FIG. 7 including the movement that occurs when a pulling force is applied.

FIG. 9 is a side view of the illustrative catheter anchoring device as applied to the cross-section of the patient of FIG. 7 including the movement that occurs when a pushing force is applied.

DETAILED DESCRIPTION

Figure 1:
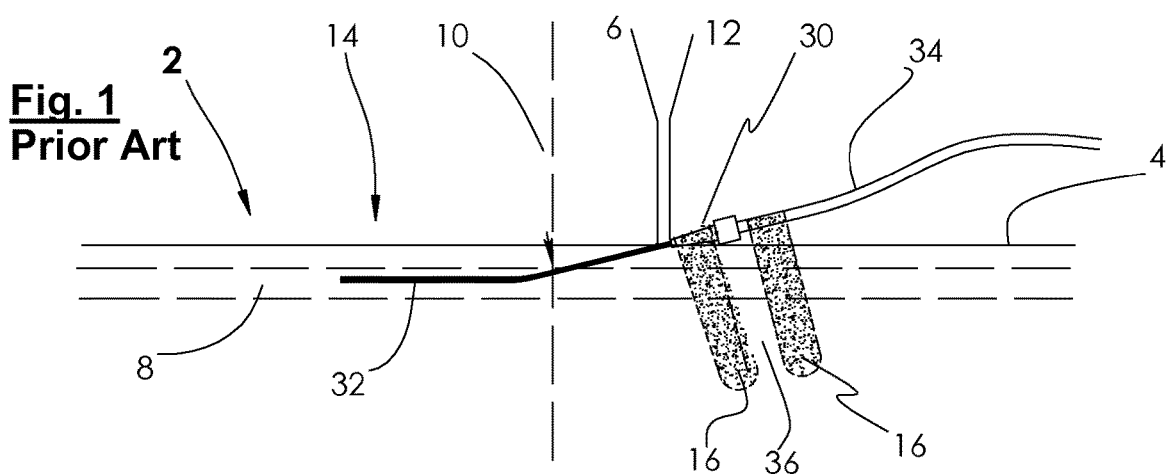
FIG. 1 is a side view of an example of the prior art attachment of an IV catheter to a patient as applied to a cross-section of the patient (e.g., an arm).

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Reviewing the prior art in FIGS. 1-4 shows an IV catheter 32 that has been placed into a vein 8 in a patient's arm 2. A catheter hub 30 and IV tubing 34 of the catheter 32 have been secured to the skin 4 of the arm 2 adjacent the catheter hub 30 with adhesive tape 16. While there are many variations of taping techniques and hundreds of patents and patents pending on devices for securing medical catheters, all of them rely on adhesively attaching the catheter hub 30 to the skin 4 adjacent the catheter hub 30.

Referring to FIG. 1 of the prior art, the catheter 32 pierces the skin 4 at the skin puncture site 6. The catheter 32 then pierces the vein 8 at the vein puncture site 10. The catheter 32 traverses a distance through the subcutaneous connective tissue from the skin puncture site 6 to the vein puncture site 10. In this example, that distance may be approximately 0.5-0.75 inches. Therefore, if the catheter 32 is 1.25 inches long, a common IV catheter length, only 0.5-0.75 inches of the catheter 32 is in the vein 8 under normal conditions, as illustrated by the distance between 10 and 14.

To understand the various movements associated with the prior art, we will assume that the vein puncture site 10 is relatively stationary and can be used as a stable reference location for relative movement comparison. Various movements and positions may be shown in the drawings for different elements. Like element numbers are used to describe like features. For example, element numbers followed by an alphanumeric character may represent the same element in different movements and positions as shown in various Figures. For example 12 and 12a may be directed to different positions or movements. Therefore, the element number followed by the alphanumeric character may be shown in the drawing but may not be completely re-described herein each time.

Figure 2:
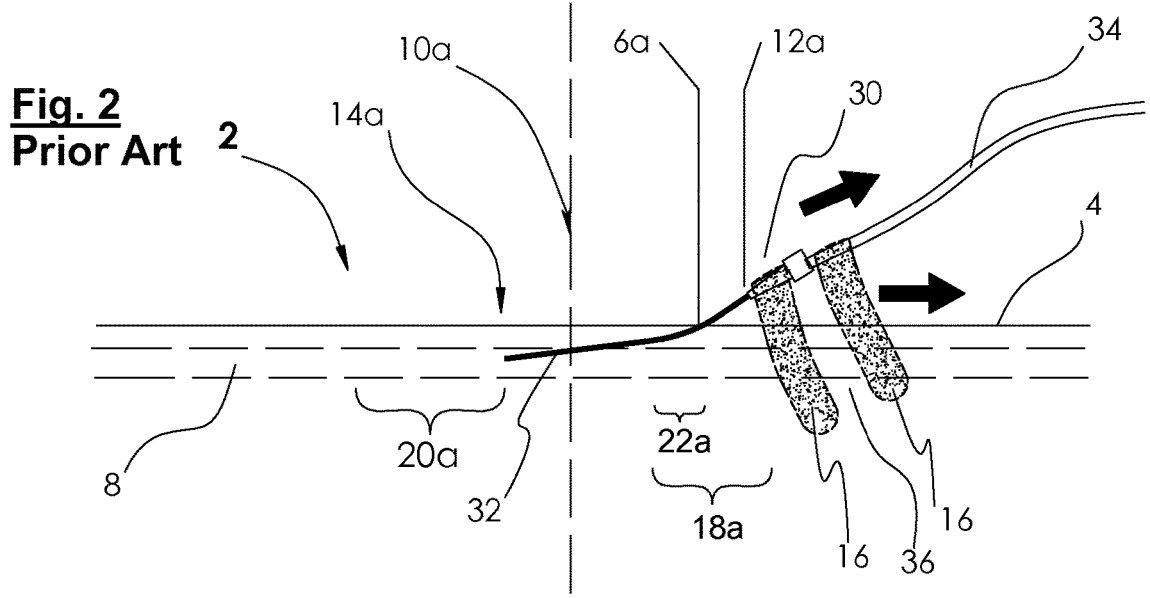
FIG. 2 depicts the prior art attachment of the IV catheter to the patient of FIG. 1 including the movement that occurs when a pulling force is applied.

FIG. 2 of the prior art shows the same IV catheter 32 as in FIG. 1 except that a pulling force (accidental perhaps) has been applied to the catheter hub 30, the IV tubing 34 or the skin 4 of the arm 2 adjacent the catheter hub 30 (e.g., at 36). The catheter hub 30 responds to the pulling action by moving from 12 (FIG. 1) to 12a (FIG. 2), which is a distance of 0.5 inches or more as illustrated as 18a (for example). At this point, 0.25 inches of the proximal end of sterile catheter 32 is outside of the skin 4, exposed to the skin bacteria. The other 0.25 inches of movement occurs from stretching the skin from 6 (FIG. 1) to 6a (FIG. 2) for a total movement of 0.5 inches relative to the vein puncture site 10. Similarly, the tip 14 position of catheter 32 has been pulled from tip 14 position 14 (FIG. 1) to position 14a (FIG. 2), a distance of greater than 0.5 inches as illustrated by 20a. The tip 14 position of catheter 32 is now at 14a and is only 0.25 inches away from popping out of vein 8 at the vein puncture site 10a. The 0.25 inch movement of the proximal catheter out of the skin is less than the 0.5 inch movement of the catheter 32 out of the vein puncture site 10 because the skin 4 of the arm 2 adjacent the catheter hub 30 (e.g., at 36) is more stretchable and movable than the vein 8 under-laying the skin on the other side of the skin puncture site 6.

Figure 3:
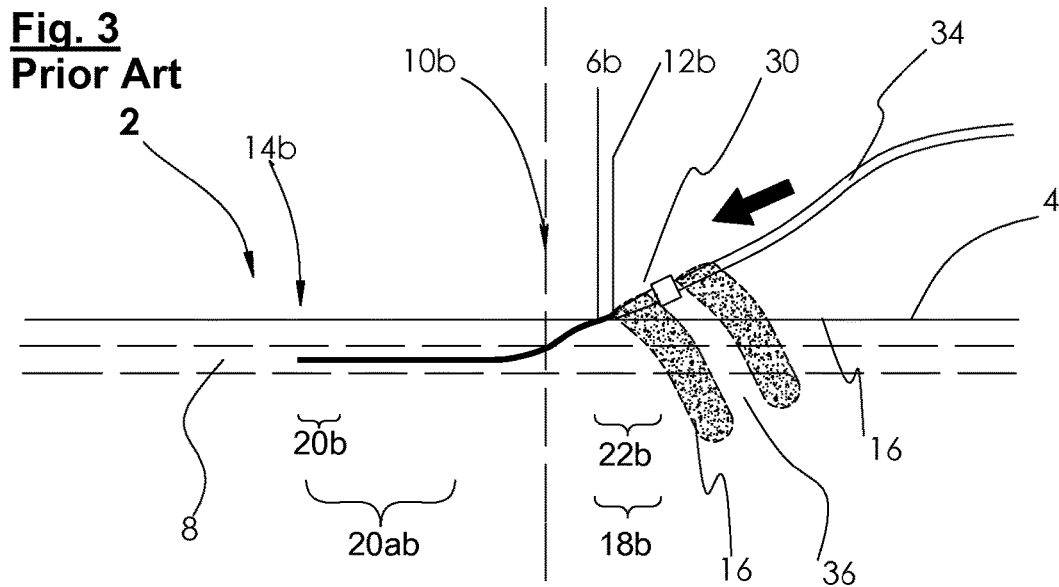
FIG. 3 depicts the prior art attachment of the IV catheter to the patient of FIG. 1 including the movement that occurs when a pushing force is applied.

FIG. 3 of the prior art shows the same IV catheter 32 as in FIG. 1 except that a pushing force (accidental perhaps) has been applied to the catheter hub 30, the IV tubing 34 or the skin 4 of the arm 2 adjacent the catheter hub 30 (e.g., at 36). Catheter hub 30 moves from 12 (FIG. 1) to 12b (FIG. 3), which is a distance of 0.25 inches or more as illustrated by 18b for example. Similarly, the tip of catheter 32 has advanced 0.25 inches in vein 8 from tip 14 position 14 to position 14b (e.g., 20b). The total movement of the tip 14 of catheter 32 from a condition of being pulled to being pushed is illustrated by 20ab, which may be a movement of as much as 0.75 inches. Therefore, typical movement of the catheter hub 30 can result in a 0.75 inch pistoning movement of the catheter tip 14 as it slides back and forth in the vein 8. The 0.75 inch pistoning movement causes scraping and denuding of the walls of vein 8. On occasion the pistoning movement results in perforation of the wall of the vein 8 with the catheter tip 14, causing a "blown IV."

Figure 4:
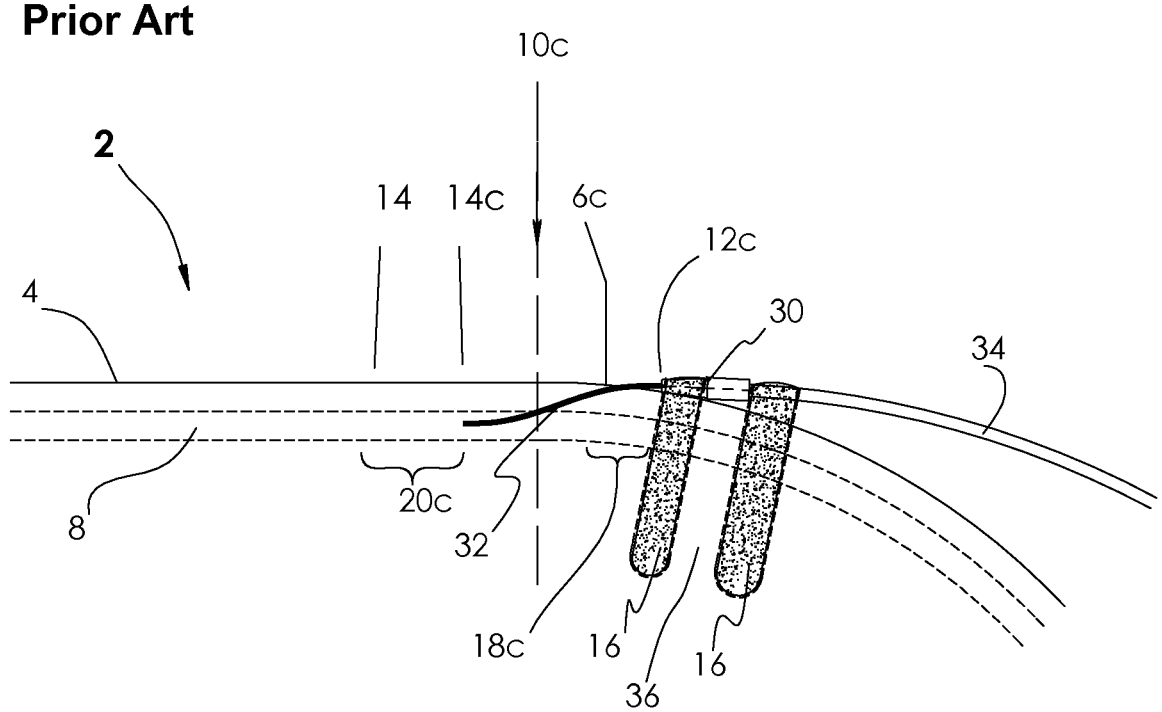
FIG. 4 depicts the prior art attachment of the IV catheter to the patient of FIG. 1 including the movement that occurs when a pulling force, such as a bending of the patient's wrist, is applied.

FIG. 4 of the prior art shows the same IV catheter 32 as in FIG. 1 except that the functional equivalent of a pulling force has been created by flexing the wrist downward. When the catheter hub 30 is attached to the skin of the wrist adjacent the hub (e.g., at 36), the catheter hub 30 moves from position 12 (FIG. 1) to position 12c (FIG. 4), which may be a distance of 0.25 inches or more. Similarly, the tip 14 of catheter 32 moves at least that far and probably further due to the difference between the movement of the skin 4 and the vein 8.

The in-and-out movement of the catheter 32 that is allowed by securing the catheter hub 30 to the skin adjacent the hub (e.g., at 36), is referred to herein as "pistoning." As previously noted, this pistoning movement can cause a number of adverse events and complications. The tip 14 of catheter 32 may pop out of the vein 8 at the vein puncture site 10 resulting in a "blown IV." The pistoning movement of up to 0.75 inches can result in the tip of the catheter 32 poking through the wall of the relatively fragile vein 8. The pistoning movement causes the catheter 32 to pull out of the skin 4 by 0.25 inches or more, where it is exposed to the bacteria growing in the blood and protein-rich serum that has oozed from the skin puncture site 6. The bacteria coat the sterile catheter 32 and then are carried under the skin 4 into the subcutaneous tissue with the next pistoning movement, where they can start a catheter or "line" infection. Line infections are a common cause for the discontinuation of IVs. Finally, the pistoning movement may cause the tip 14 of catheter 32 to abrade the endothelial lining of the wall of vein 8, increasing the chances of venous thrombosis (blood clotting) to occur. All of these adverse events and complications occur because the catheter hub 30 of the catheter is secured to the skin 4 adjacent the hub (e.g., at 36), as in the prior art.

The instant invention is fundamentally different from the prior art in that the skin attachment portion 52 is primarily attached to the skin 4 over-laying and lateral to the subcutaneous catheter 32. This skin attachment location is on the opposite side of the skin puncture site from the prior art.

Figure 5:
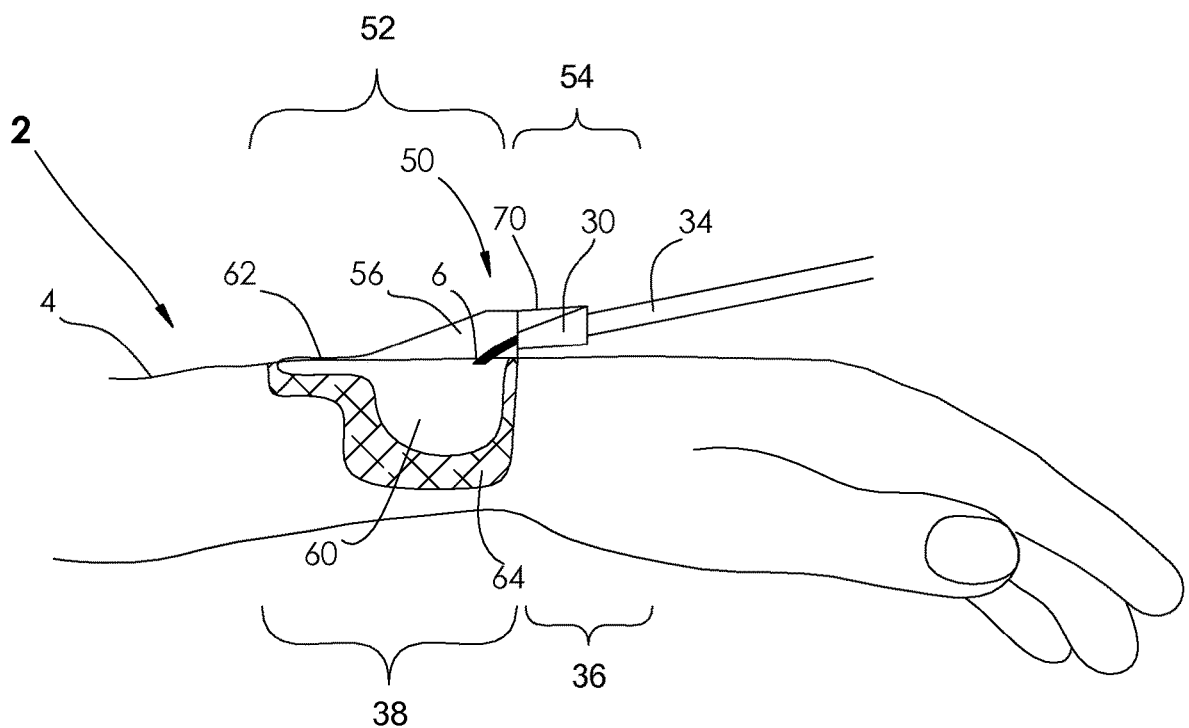
FIG. 5 is side view of an illustrative embodiment of a catheter anchoring device.
Figure 6:
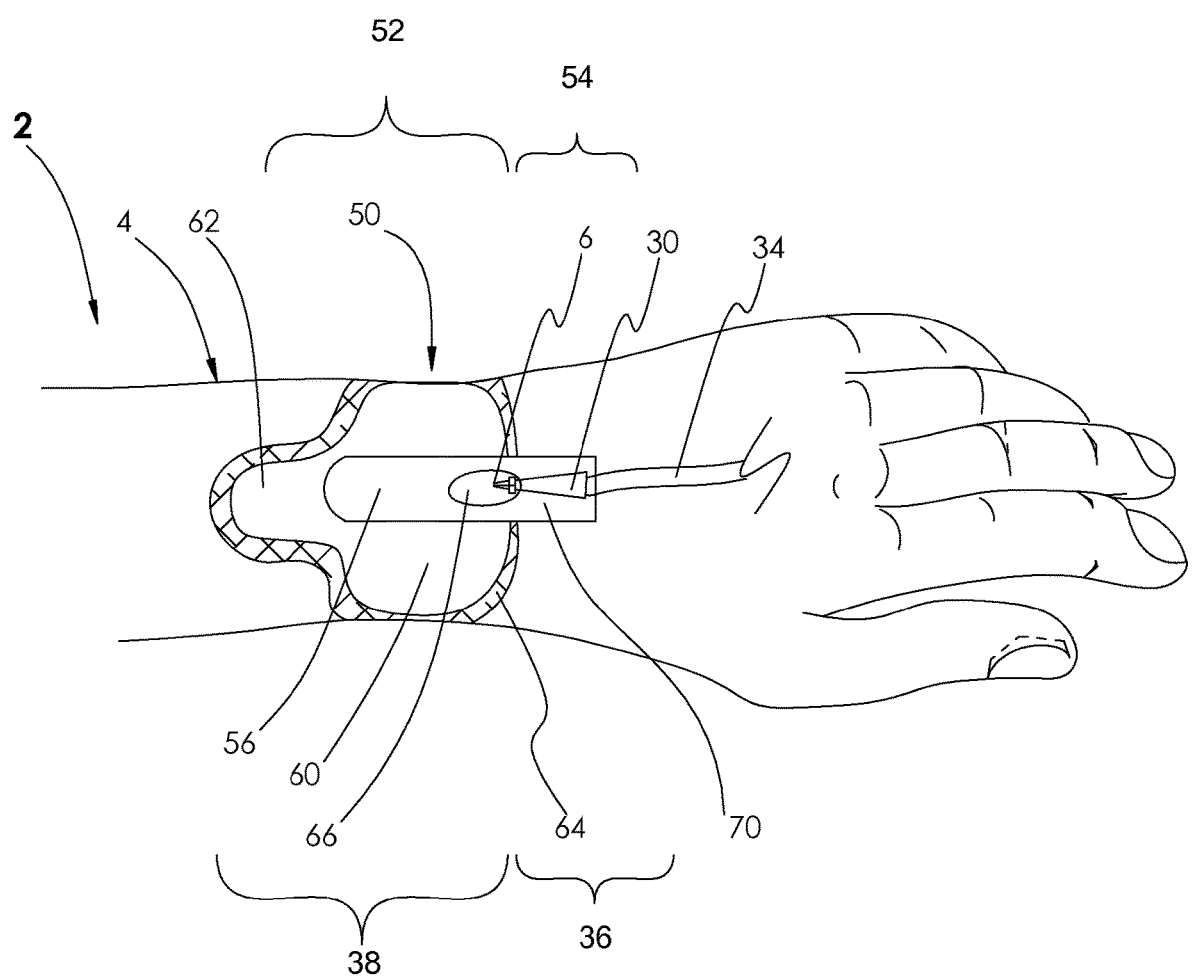
FIG. 6 is a top view of the illustrative catheter anchoring device of FIG. 5.

Referring now to FIGS. 5 and 6 and also FIGS. 7-10. Some embodiments of the catheter anchoring device 50 of the instant invention comprise two portions. The skin attachment portion 52 and the catheter capture portion 54.

In some embodiments, the skin attachment portion 52 includes a structural body 56 and one or more skin attachment wings 60 and 62. The skin attachment portion 52 may also include an adhesive tape layer 64 interposed between the patient's skin 4 and the structural body 56 and the skin attachment wings 60, 62 when in use.

The skin attachment portion 52 attaches to the skin 4 of the arm 2 above and lateral to the subcutaneously located catheter (e.g., at 38). This is on the opposite side of the skin puncture site 6 compared to the prior art attachment to the skin 4 of the arm 2 adjacent the catheter hub 36.

In some embodiments, the catheter capture portion 54 is attached to the structural body 56 and extends to the opposite side of the skin puncture site 6 in order to capture and hold the catheter hub 30. A key aspect to this catheter anchoring device 50 is that it does not need to be attached to the skin 4 of the arm adjacent to catheter hub 30 (e.g., at 36). In some embodiments there may be a loose attachment to the skin 4 of the arm 2 adjacent the catheter 34, however, the principal attachment is to the skin 4 of the arm 2 above and lateral to the subcutaneously located catheter 32 (e.g., at 38 in FIGS. 5 and 6). This design allows the catheter hub 30 to be securely captured and held, yet remains relatively independent of the skin 4 of the arm 2 adjacent the catheter hub 30 (e.g., at 36).

In other words, the catheter anchoring device 50 of the embodiment of FIGS. 5-10, as well as other embodiments for securing percutaneous medical catheters to the skin 4 of the body may include the catheter capture portion 54 and the skin attachment portion 52. The catheter capture portion 54 may be configured to engage with a portion of the catheter 32 (e.g., FIGS. 7-10) protruding from the skin 4 after percutaneous placement of the catheter 32 into the body. The skin attachment portion 52 is coupled to the catheter capture portion 54.

In some embodiments the skin attachment portion 52 has a upper surface 61a (e.g., a first surface), a lower surface 61b (e.g., a second surface), and an adhesive layer 64. The upper surface 61a configured to face away from the skin 4 of the body (e.g., arm 2) when the catheter anchoring device 50 is positioned to anchor the catheter 32 to the body (e.g., arm 2). The lower surface 61b located opposite the upper surface 61a and configured to face the skin 4 of the body when the catheter anchoring device 50 is positioned to anchor the catheter 32 to the body (e.g., arm 2). The adhesive layer 64 may be disposed on the lower surface 61b. The adhesive layer 64 may be configured to adhesively attach the lower surface 61b of the skin attachment portion 52 to the skin 4. In some embodiments, the adhesive layer 64 is disposed on the lower surface 61b of the skin attachment portion 52 and is configured to anchor the catheter anchoring device 50 to the body at the skin 4 overlaying the subcutaneously located catheter 32 and lateral to the subcutaneously located catheter 32 (e.g. at 38 in FIGS. 5 and 6).

In some embodiments of the catheter anchoring device 50, when the adhesive layer 64 is applied to the skin 4 to anchor the device, a second portion of the catheter, or IV tubing 34 that may extend outside of the catheter hub 30 (if provided) and away from the skin puncture site 6 is located more distal from the skin 4 (e.g., at 36 in FIGS. 5 and 6) than the adhesive layer 64 (e.g., at 38 in FIGS. 5 and 6).

FIGS. 7-10 demonstrate the same relative movements as FIGS. 1-4 demonstrated for the prior art. FIGS. 7-10, the vein puncture site 10 will also be used as a general reference point between the Figs. However with the instant invention of the vein puncture site 10 also moves in response to movement of the catheter anchoring device 50. This is in contrast to the prior art where the vein puncture site 10 is relatively stationary despite movement of the catheter hub 30.

FIG. 7 shows a vertical cross section of the catheter anchoring device 50 attached to the skin 4 of a the patient's arm 2. In some embodiments the skin attachment portion 52 is adhesively attached to the patient's arm 2 by way of lateral skin attachment wings 60. The primary attachment is to the skin 4 of the arm 2 above and lateral to the subcutaneous catheter 32, which in FIG. 7 is under the skin 4 to the left of the skin puncture site 6. In some embodiments, the primary attachment may be directly above, or directly overlay the subcutaneously placed catheter 32 (e.g., at 38 in FIGS. 5 and 6).

FIG. 8 demonstrates the results of a 0.5 inch pulling movement on the IV tubing 34. The catheter anchoring device 50 moves 0.5 inches to the right. Because the catheter anchoring device 50 is attached to the skin 4 of the arm 2 above and lateral to the catheter 32, the skin puncture site 6 also moves 0.5 inches to 6*d*, a movement represented by 22*d*. The key is that there is no net movement between the skin puncture site 6*d* and the catheter/hub junction 12*d*. Therefore, there is no pistoning of the catheter 32, in and out of the skin puncture site 6 when the catheter anchoring device 50 is moved in the direction that would pull the catheter 32 out of the skin 4 if anchored by the prior art devices. The distance and direction that the vein 8 and the vein puncture site 6 move in response to the overlaying catheter anchoring device being pulled "out" is depicted by 24*d*. Here, the movement of the catheter tip 14 relative to the vein 8 is minimized.

Because the catheter anchoring device 50 is attached to the skin 4 of the arm 2 above and lateral to the catheter 32 (e.g., at 38 in FIGS. 5 and 6), the skin puncture site 6, a movement of the skin attachment portion 52, 0.5 inches to the right, results in a movement of the underlined vein 8 at least 0.25 inches in the same direction (the vein 8 is loosely attached to the overlying skin 4). Therefore the vein puncture site 10 is moved to 10*d*. The 0.5 inch movement of the catheter anchoring device 50 results in only a 0.25 inch retraction of the catheter 32 out of the vein puncture site 10*d*. Similarly, the 0.5 inch movement of the catheter tip 14 position from 14 (FIG. 7) to 14*d* (FIG. 8), resulted in only a 0.25 inch movement relative to the adjacent vein 8 wall, because the vein 8 moved 0.25 inches in the same direction. Since the vein 8 moves in the same direction as the general movement of the catheter anchoring device 50, both the chance of the catheter tip 14 popping out of the vein puncture site 10 and the chance of abrasion and/or puncturing of the wall of vein 8 adjacent to the catheter tip 14 are markedly reduced.

FIG. 9 demonstrates the results of a movement of the catheter anchoring device 50, 0.5 inches into the vein 8 (to the left). The catheter/hub junction moves from position 12 to 12*e* (FIG. 9), pushing the skin puncture site 6 to 6*e*. Because the catheter anchoring device 50 is attached to the skin 4 of the arm 2 above and lateral to the catheter (e.g., at 38 in FIGS. 5 and 6), a movement of the skin attachment portion 52, 0.5 inches to the left, results in a movement of the underlying vein 8 at least 0.25 inches in the same direction (the vein 8 is loosely attached to the overlying skin 4). Therefore the vein puncture site 10 is moved to 10*e*. The 0.5 inch movement of the catheter anchoring device 50 results in only a 0.25 inch introduction of the catheter 32 into the vein puncture site 10*e*. Similarly, the 0.5 inch movement of the catheter tip 14 from 14 (FIG. 7) to 14*e*, resulted in only a 0.25 inch movement relative to the adjacent vein 8 wall, because the vein 8 moved 0.25 inches in the same direction. Since the vein 8 moves in the same direction as the general movement of the catheter anchoring device 50, the chance of abrasion and/or puncturing of the wall of vein 8 adjacent to the catheter tip 14 is markedly reduced. The distance and direction that the vein 8 and the vein puncture site 6 move in response to the overlaying catheter anchoring device being pushed "in" is depicted by 24*e*. Here, the movement of the catheter tip 14 relative to the vein 8 is also minimized.

Figure 10:
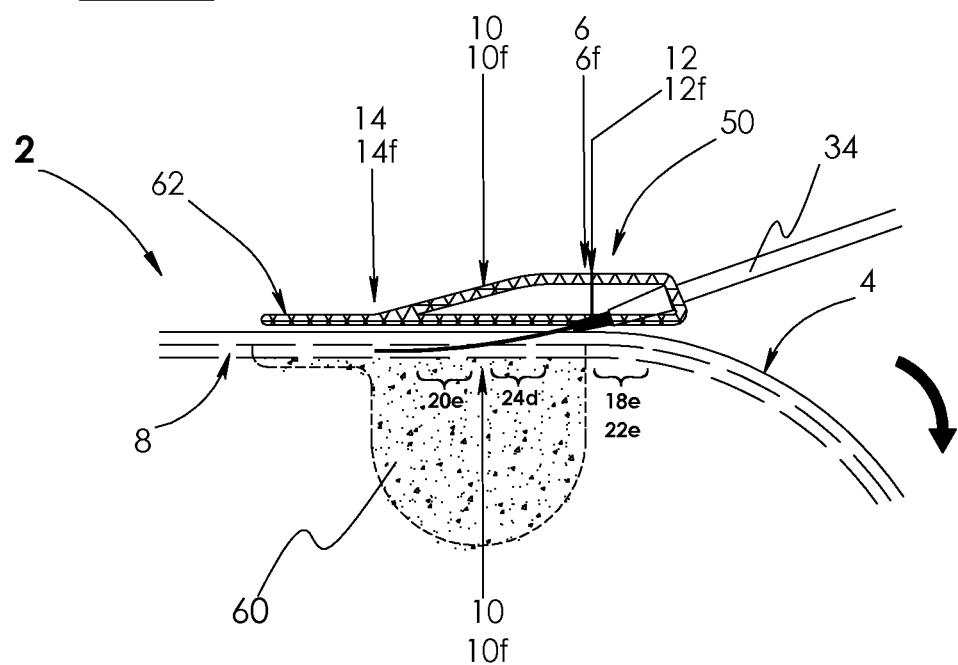
FIG. 10 is a side view of the illustrative catheter anchoring device as applied to the cross-section of the patient of FIG. 7 including the movement that occurs when a pulling force, such as a bending of the patient's wrist, is applied.

FIG. 10 demonstrates the relative movement of the catheter anchoring device 50 as a result of the flexion of the wrist. Because there is no connection between the catheter hub 30 and the skin 4 of the arm 2 adjacent the catheter hub 30, flexion of the wrist does not result in any movement of the catheter anchoring device 50 relative to the skin puncture site 6 versus 6*f*, the vein puncture site 10 versus 10*f*, or the catheter tip 14 abrading/puncturing the vein 8 wall e.g., 14 versus 14*f*.

It is evident that all of these relative movements are significantly reduced or eliminated by the catheter anchoring device 50 being attached to the skin 4 of the arm 2 above and lateral to the subcutaneous catheter 32. This is in contrast to the prior art where the catheter hub 30 is attached to the skin 4 of the arm 2 adjacent the catheter hub 30.

As shown in FIGS. 5 and 6, in some embodiments, this catheter anchoring device 50 includes a structural body 56 that forms the "backbone" of the device and substantially overlays the subcutaneous catheter 32. In some embodiments, the structural body 56 comprises a "half pipe" structure with a rounded upper surface and the open interior straddling and parallel to the subcutaneous catheter 32. The structural body 56 provides longitudinal rigidity to the device for transferring forces from the catheter capture portion 54 to the skin attachment portion 52. In some embodiments, the structural body 56 lies substantially in the center of the skin attachment portion 52 effectively creating a "center of effort" for externally applied force dissipation.

Figure 17:
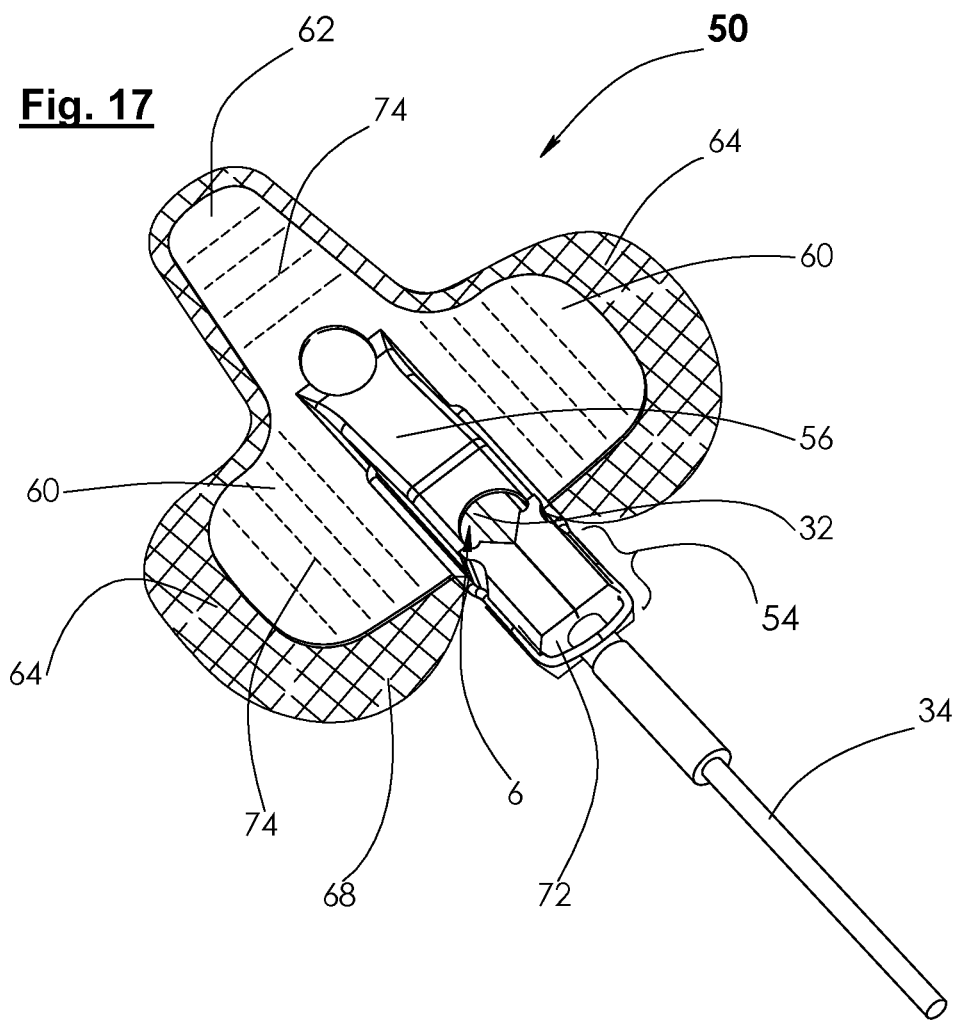
FIG. 17 is a top perspective view of a fourth illustrative embodiment of a catheter anchoring device.
Figure 19:
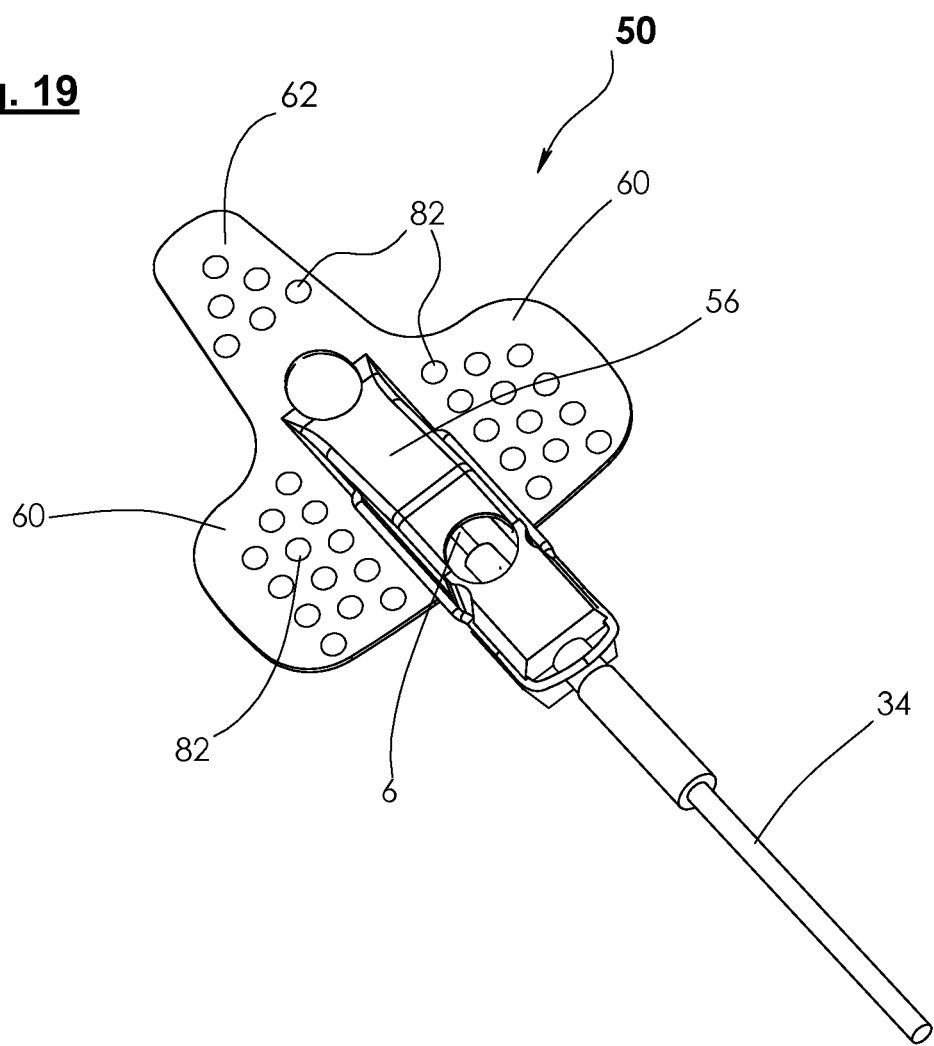
FIG. 19 is a top perspective view of a sixth illustrative embodiment of a catheter anchoring device.

In some embodiments two or more flexible skin attachment wings 60, are attached to the lateral sides of the structural body 56. One of the key features of the attachment wings 60 is that they must be flexible enough to conform to the contours of the patient's body and yet stiff enough to provide stability to the structural body 56 of the catheter anchoring device 50. In some embodiments the lateral skin attachment wings 60 are made of a layer of plastic material. The flexibility of the wings 60 may be enhanced by making the plastic wings 60 thin, or by including a series of hinges 74 or "living hinges" or grooves that preferentially flex and bend (as shown in FIG. 17), or by adding an array of holes 82 (FIG. 19) passing through the wing 60 to physically remove material from the wing 60 creating a weakened bend area (as shown in FIG. 19). In some embodiments, the flexibility of the lateral skin attachment wings 60 may be enhanced by making the wings 60 out of a softer, lower durometer, more flexible plastic or rubber material than the structural body 56.

As shown in FIG. 7, the skin attachment wings 60 may include the upper surface 61*a* (e.g., the first surface) located opposite the lower surface 61*b* (e.g., the second surface). The upper surface 61*a* may be configured to face away from the skin 4 when the device is positioned to anchor the catheter 32 to the body (e.g., arm 2, or any other suitable location) of the patient. The lower surface 61*b* may be configured to face the skin 4 of the body when the device 50 is positioned to anchor the catheter 32 to the body.

Figure 20:
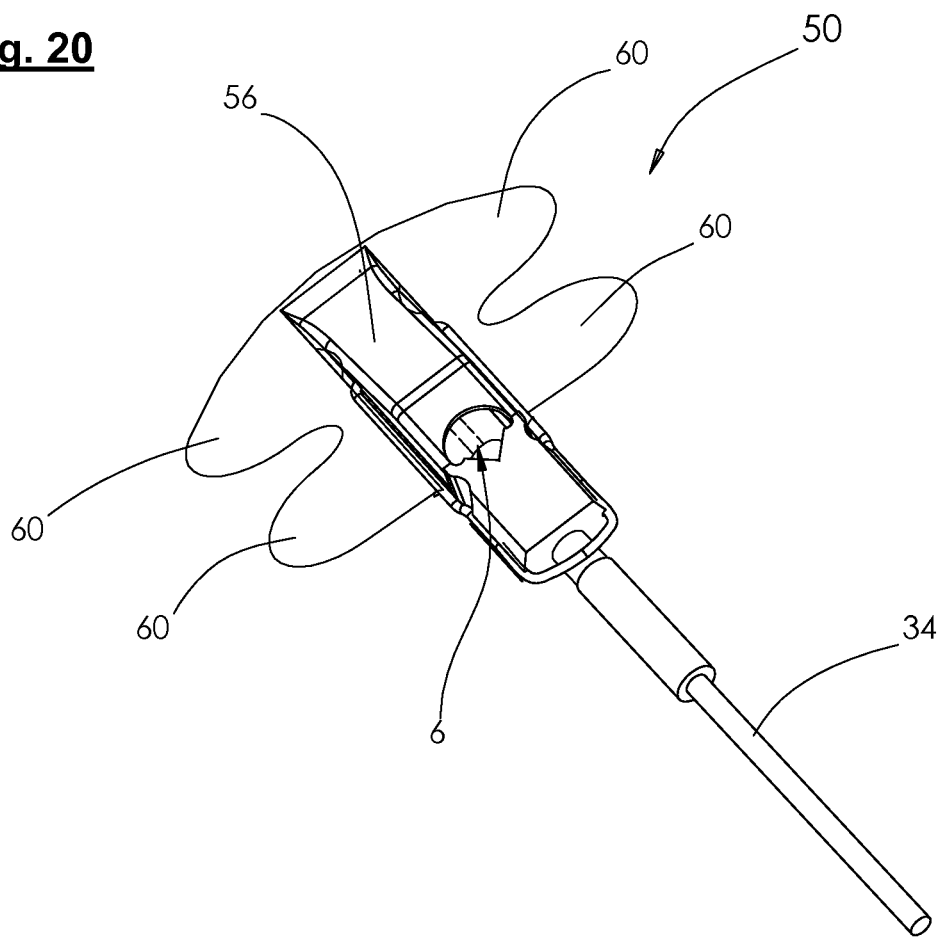
FIG. 20 is a top perspective view of a seventh illustrative embodiment of a catheter anchoring device.

The skin attachment wings 60, are designed to provide a larger surface for adhesion of the catheter anchoring device 50 to the skin 4. In some embodiments the adhesive layer 64 (e.g., FIG. 5) is applied to the lower surface 61*b* of the wings 60 for adhering the wings to the patient's skin 4 as shown in FIGS. 19 and 20. In some embodiments the adhesive is applied to the lower surface 61*b* (e.g, as previously shown in FIG. 7) of the wings to adhere the skin attachment wings 60 to a layer of adhesive tape 64 and then the tape adheres to the patient's skin 4 as shown in FIGS. 17 and 18.

In some embodiments, the adhesive layer 64 is disposed on the lower surface 61*b* and is configured to adhesively attach the lower surface 61*b* to the skin 4 such that the skin attachment portion 52 is configured to anchor the device to the body at the skin 4 overlaying the subcutaneously located catheter 32 and lateral to the subcutaneously located catheter 32 (e.g., at 38 as shown in FIGS. 5 and 6). In some embodiments, the adhesive layer 64 is configured to be located directly over the subcutaneously located catheter 32 proximate and/or surrounding the skin 4 puncture site (e.g., 6 in FIG. 7) when anchoring the device 50 with the catheter properly inserted. In some embodiments the adhesive layer 64 placement may be configured to surround and/or seal around the puncture site 6, or may be configured to surround at least 270 degrees around the skin puncture site 6. In some embodiments the skin puncture site is surrounded on opposite sides of the puncture site laterally. In other words, some embodiments surround 180 degrees of the puncture site.

Figure 18:
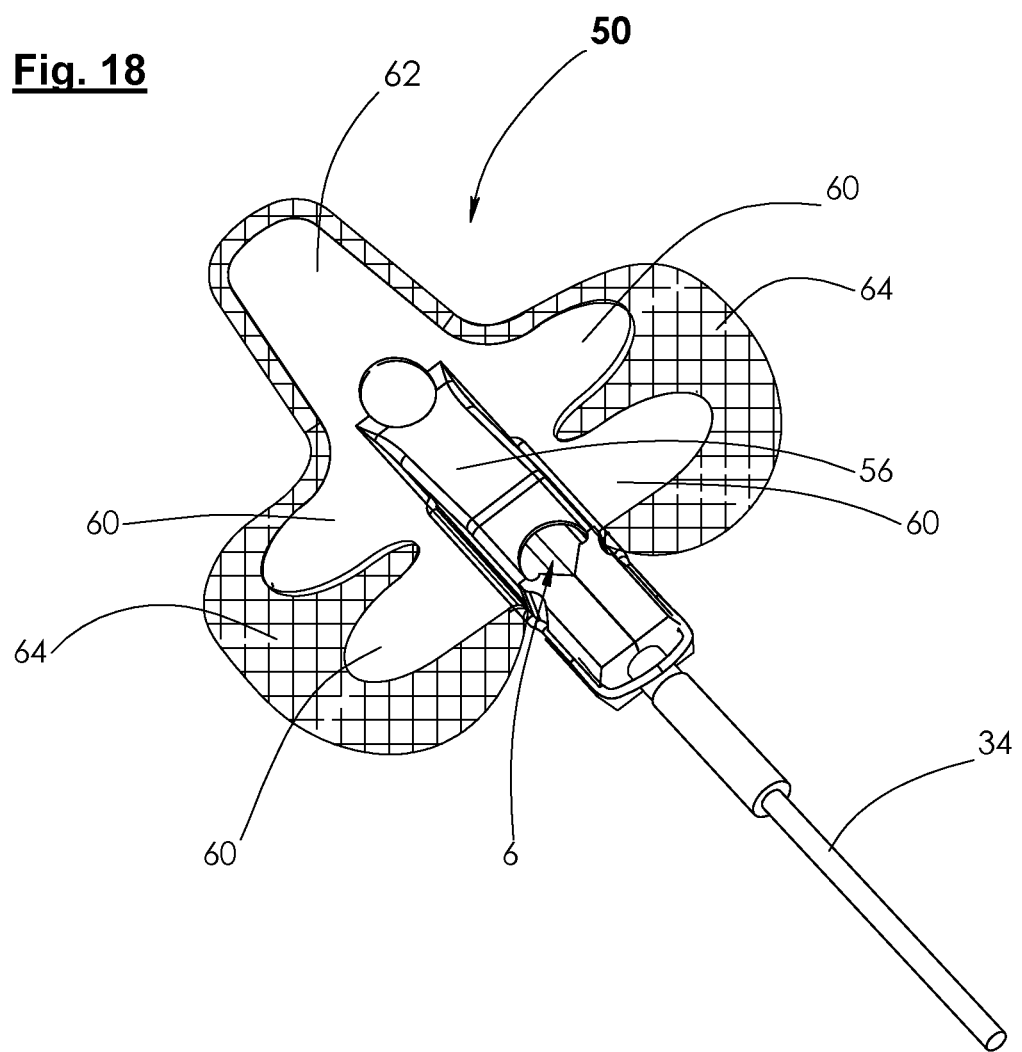
FIG. 18 is a top perspective view of a fifth illustrative embodiment of a catheter anchoring device.

In some embodiments, as shown in FIGS. 17-19, the catheter anchoring device 50 includes a third skin attachment wing extending longitudinally from the structural body 56 and overlaying the tip 14 of the subcutaneous catheter 32. The construction of the longitudinal skin attachment wing 62 may be similar to the lateral skin attachment wings 60. The longitudinal skin attachment wing 62 also has an adhesive layer 64 applied to its lower side that may be attached to the patient's skin 4, such as a layer of adhesive 64 tape which may be attached to the patient's skin 4.

In some embodiments, the purpose of the longitudinal skin attachment wing 62 is to provide added stability to the catheter anchoring device 50. Additionally, since the longitudinal skin attachment wing 62 adhesively attaches to the skin 4 overlaying the tip 14 of the subcutaneous catheter 32 as shown in FIGS. 7-9, a movement of the catheter anchoring device 50 and catheter 32 will cause a similar movement of the skin 4 overlaying the subcutaneous catheter tip 14, and a similar movement of the vein 8 that is loosely attached to the skin 4 overlaying the tip 14. The longitudinal skin attachment wing 62 attached to the skin 4 overlying the catheter tip 14 is therefore preferred in order to move the skin 4 overlying the catheter tip 14, the vein 8 and the catheter tip 14, all simultaneously in the same direction in response to a movement of the catheter hub 30 or IV tubing 34. The longitudinal skin attachment wing 62 must have a stiffness that allows for "pushing" the skin 4 as well as "pulling" the skin 4, in contrast to plastic film bandages that can only "pull" the skin 4. The simultaneous movement of the catheter 32 and vein 8 clearly reduces the probability of the catheter tip 14 inadvertently poking through the fragile wall of the vein 8 as a result of inadvertent movement of the catheter 32, in contrast to the prior art.

In some embodiments, and as shown in FIGS. 5, 6, 17 and 18, a layer of adhesive 64 such as adhesive tape, is located between the skin attachment wings 60, 62, and the patient's skin 4. In this case, the skin attachment wing 60, 62, is bonded to the adhesive layer 64. The bond maybe an adhesive bond, a solvent bond or a thermal bond such as a heat, RF or ultrasound.

In some embodiments, the adhesive layer 64 is made of fabric, foam, plastic film, fiber reinforced film, or any other suitable adhesive layer. The attachment of the adhesive layer 64 to the patient's skin 4 may be an adhesive that can be softened or dissolved with alcohol for easy removal from the skin. Other adhesives are anticipated including but not limited to hydrogels and hydrocolloids. The adhesive layer 64 may advantageously include nonstick release liners applied over the adhesive surface that can be removed at the time of application to the patient. The skin attachment portion 52 adhesive layer 64 may be configured to adhesively attach the anchoring device 50 to the skin 4, wherein more than 50% of the adhesive surface of the skin attachment portion 52 is attached to the skin overlaying and lateral to the subcutaneously located catheter (e.g., 38). In a preferred embodiment, more than 70% of the adhesive surface is configured to attach as described, and in a more preferred embodiment, more than 85% of the adhesive surface is attach as described. This adhesive arrangement provides a secure connection of the device 50 to the skin 4.

In some embodiments, the adhesive layer 64 or lateral skin attachment wings 60 may extend past the plane 68 of the skin puncture site 6 as shown in FIG. 17. While this configuration may add to the stability and security of the anchoring device 50, the primary attachment is still over the subcutaneous located catheter 32 and the catheter capture portion 54 is not attached to the skin 4 adjacent the catheter hub 30, in a preferred embodiment.

As shown in FIGS. 18 and 20, in some embodiments the lateral skin attachment wings 60 may be made of two or more small wings 60, to improve the flexibility and accommodation to the patient's anatomy.

In some embodiments as shown in FIG. 20, the catheter anchoring device 50 may not include a longitudinal skin attachment wing 62. This may be advantageous in the case of shorter catheters as may be used in pediatrics.

In some embodiments, and as shown in FIGS. 5 and 6, the catheter capture portion 54 is attached to the structural body 56 of the skin attachment portion 52 on the end of the structural body 56 that is opposite the longitudinal skin attachment wing 62. Any suitable attachment may be used. There are many designs, techniques and methods of capturing the catheter hub 30 or the catheter 32 which would work and are anticipated by this disclosure.

Figure 11:
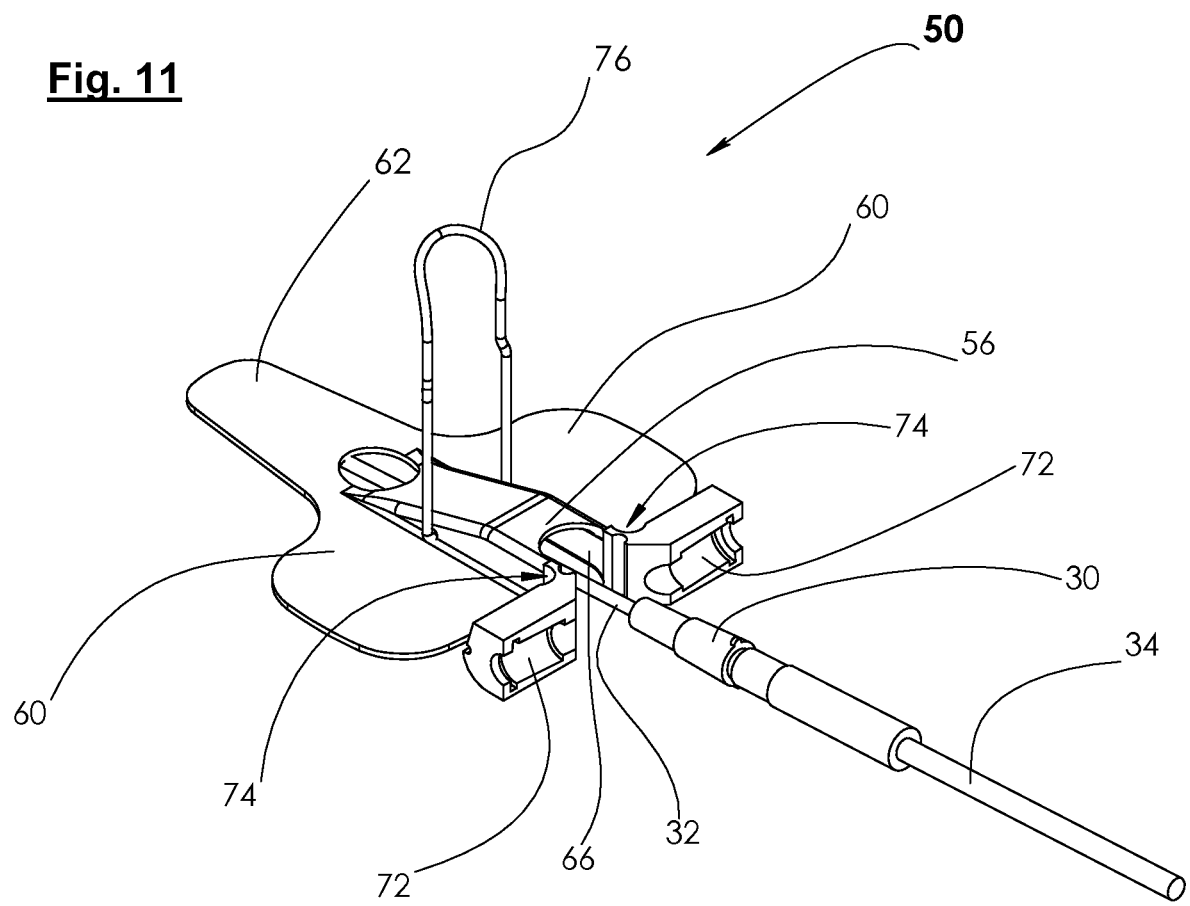
FIGS. 11-13 are top perspective views of a second illustrative embodiment of a catheter anchoring device with the catheter hub arranged in different positions (e.g., open, closed, locked).
Figure 12:
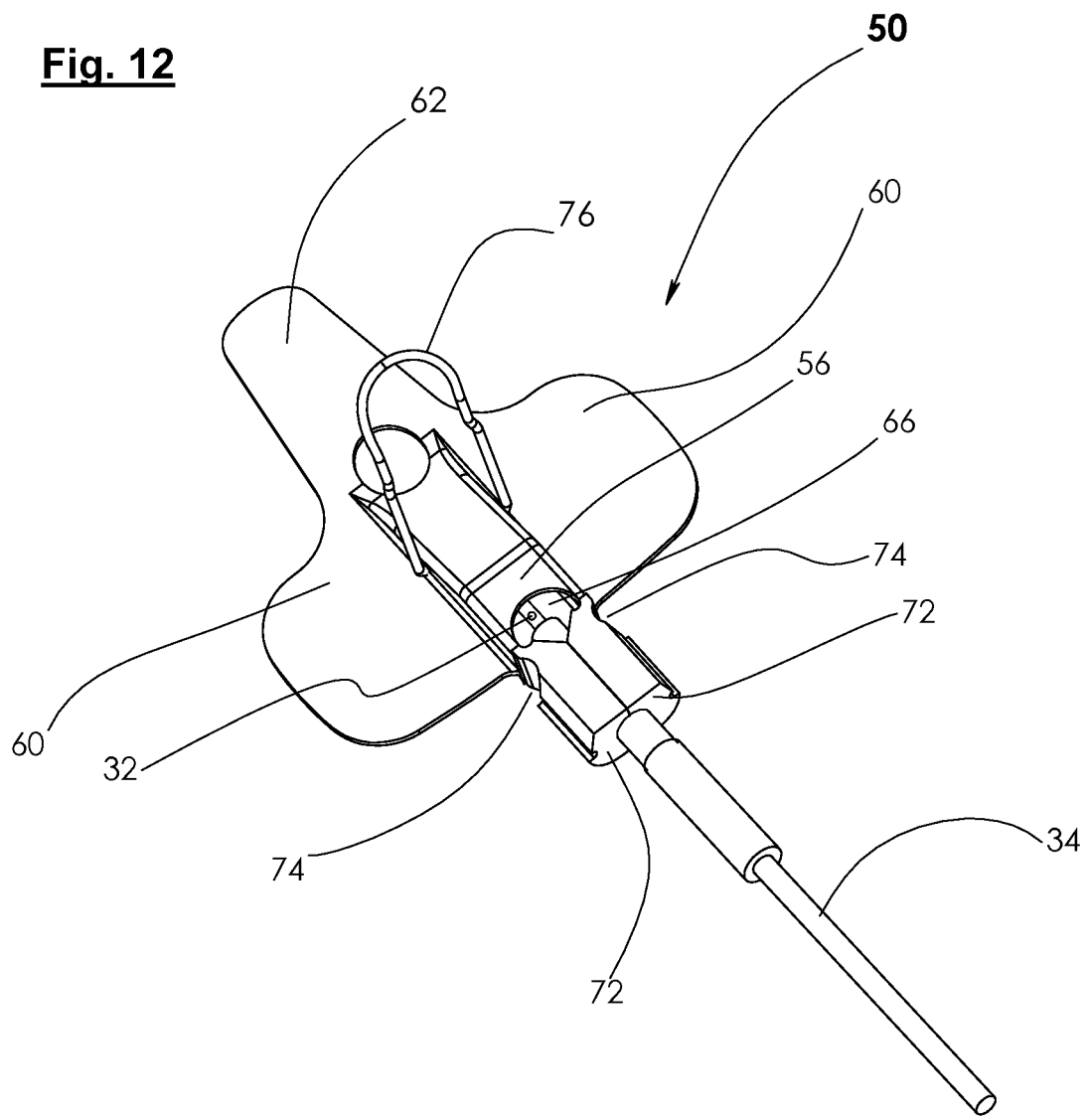
Figure 13:
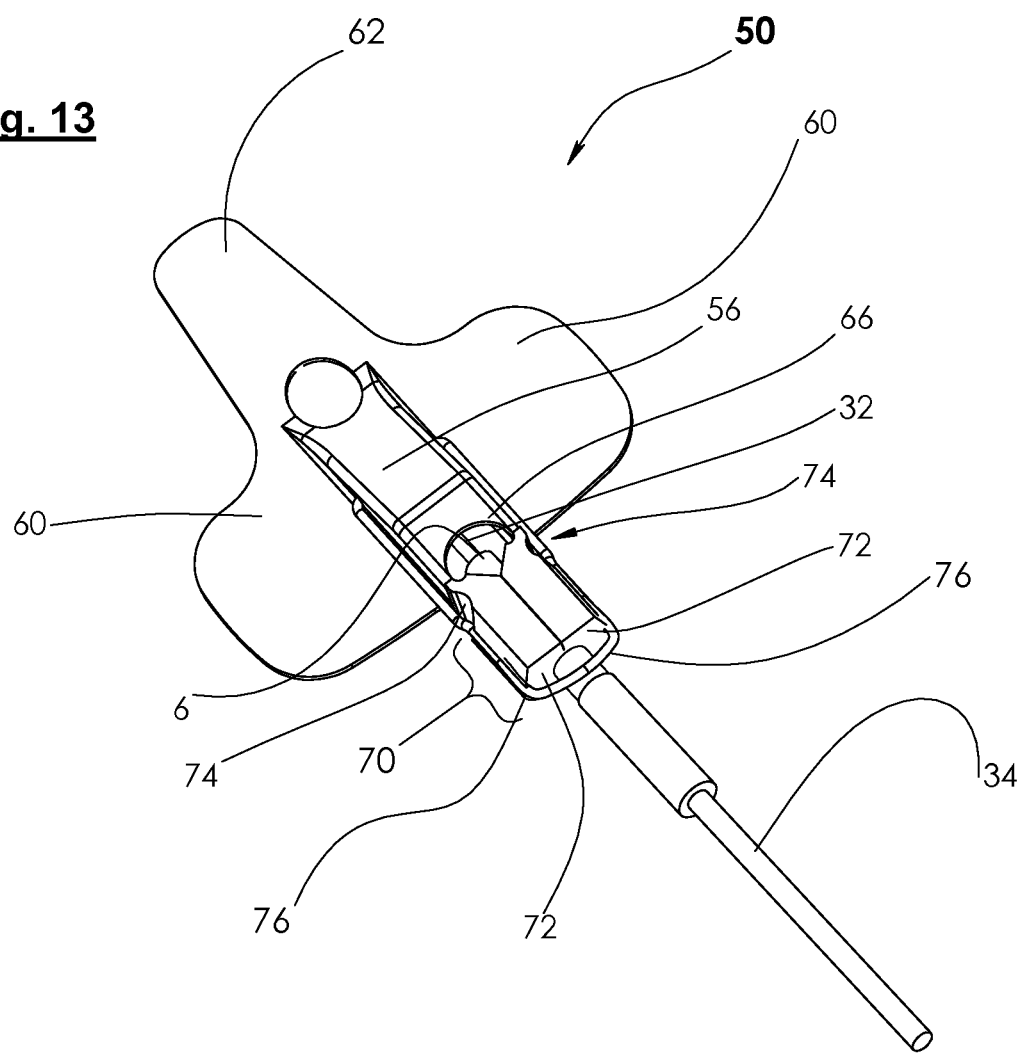

In some embodiments as shown in FIGS. 11-13, the catheter capture receptacle 70 is comprised of two pieces of half shell 72 molded plastic that "clamshell" together around the catheter hub 30 or the catheter 32. In some embodiments, the "clamshell" action can occur because of two vertically oriented hinges 74 molded at the junction between the two catheter capture receptacle half shells 72 and the structural body 56 of the skin attachment portion 52. The hinge 74 may be a "living hinge," which is a thinned line in a molded plastic part that promotes bending or hinging at that location. The vertically oriented hinges 74 may be "living hinges" that allow the two half shells 72 to swing horizontally closed from the sides as shown in FIG. 12. This allows the catheter capture receptacle 70 to close around the catheter hub 30 or the catheter 32 positively controlling the catheter hub 30, preventing its movement in any direction. The horizontal closing of the half shells 72 allows the capture of the catheter hub 30 without displacing the newly inserted catheter by lifting it. This is in contrast to tape and prior art anchoring devices, all of which require that the hub 30 be elevated off of the skin 4 so that the tape or anchoring device can be inserted between the hub 30 and the skin 4. This lifting movement of the catheter hub 30 obviously increases the probability of dislodgment of the catheter 32 during the securing procedure.

In some embodiments as shown in FIGS. 11-13, a U-shaped piece of wire or metal may be adapted to snap around the two half shells to form a catheter capture receptacle lock 76. When snapped into a closed position as shown in FIG. 13, the U-shaped wire holds the two half shell components 72 of the catheter capture receptacle 70 in a closed and locked position. In some embodiments, the U-shaped receptacle lock 76 (e.g., wire) is adapted to also lie against the vertical sides of the structural body 56. In this location the U-shaped receptacle lock 76 provides additional longitudinal stability and strength between the skin attachment portion and the catheter capture portion, traversing across the hinge 74 junction between the two portions. Although the receptacle lock 76 is described as a U-shaped piece of wire or metal, other suitable shapes, and other suitable materials that provide the same locking function, including plastics and V-shaped locks, may be provided and still fall within the scope of this disclosure.

In some embodiments, as shown in FIGS. 11-16, the U-shaped receptacle lock 76 is adapted to hinge from the structural body 56 with a horizontally oriented hinge mechanism. This allows the U-shaped receptacle lock 76 to swing in an up and down motion, swinging downward to lock the two half shells 72 that swing closed from the sides. The hinging mechanisms of these two components (the half shells 72 and the receptacle lock 76) are oriented perpendicularly to each other and therefore result in a strong, inflexible joint when closed and locked together.

The strength and inflexibility of vertically oriented hinges 74 of the catheter capture receptacle 70 and a horizontally oriented hinge of the receptacle lock 76 positively captures the catheter hub 30 or catheter 34 and prevents any twisting movements of the catheter hub 30 or catheter 34. The catheter hub 30 is effectively attached to the end of a lever (the structural body 56) and the entire lever would need to twist in order for the catheter hub 30 to twist. In some embodiments, the receptacle lock 76 snaps into a groove in the side of the catheter capture receptacle 70. This creates a secure locking mechanism that, in some embodiments, can only be opened by prying the receptacle lock 76 up with an instrument. Small protuberances may be included on the sides of the half shells 72 for easy grasping with two fingers, in order to aid in snapping the receptacle lock 76 into the closed position with the thumb.

Figure 14:
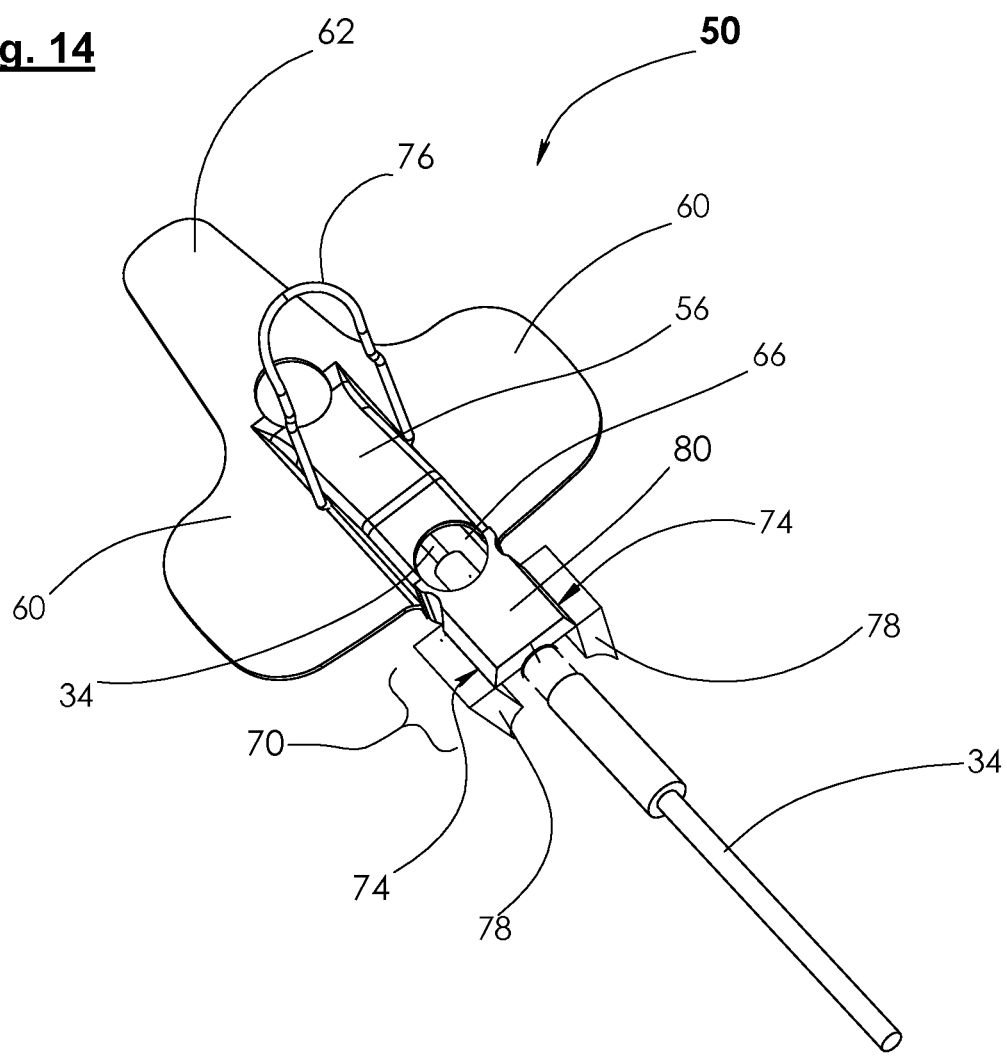
FIGS. 14-16 are top perspective views of a third illustrative embodiment of a catheter anchoring device with the catheter hub arranged in different positions (e.g., open, closed, locked).
Figure 15:
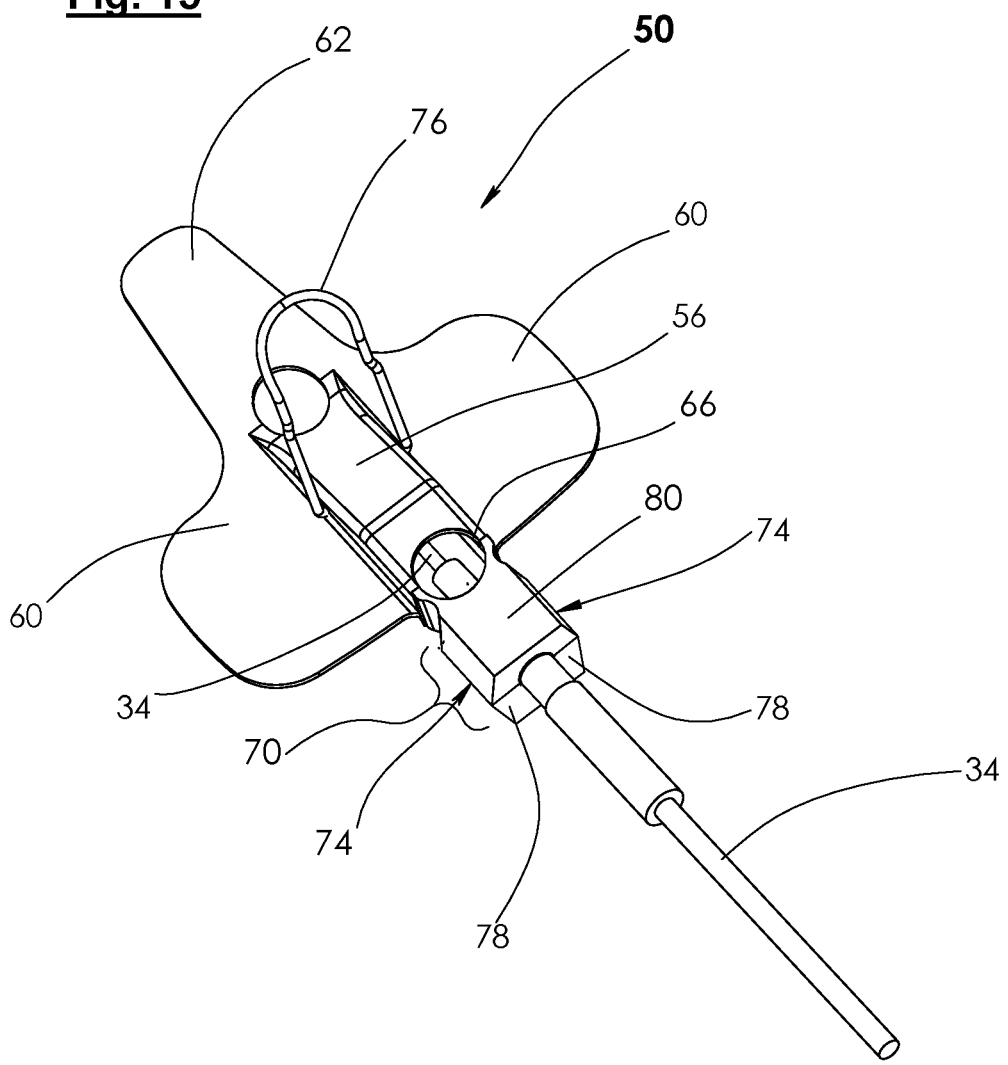
Figure 16:
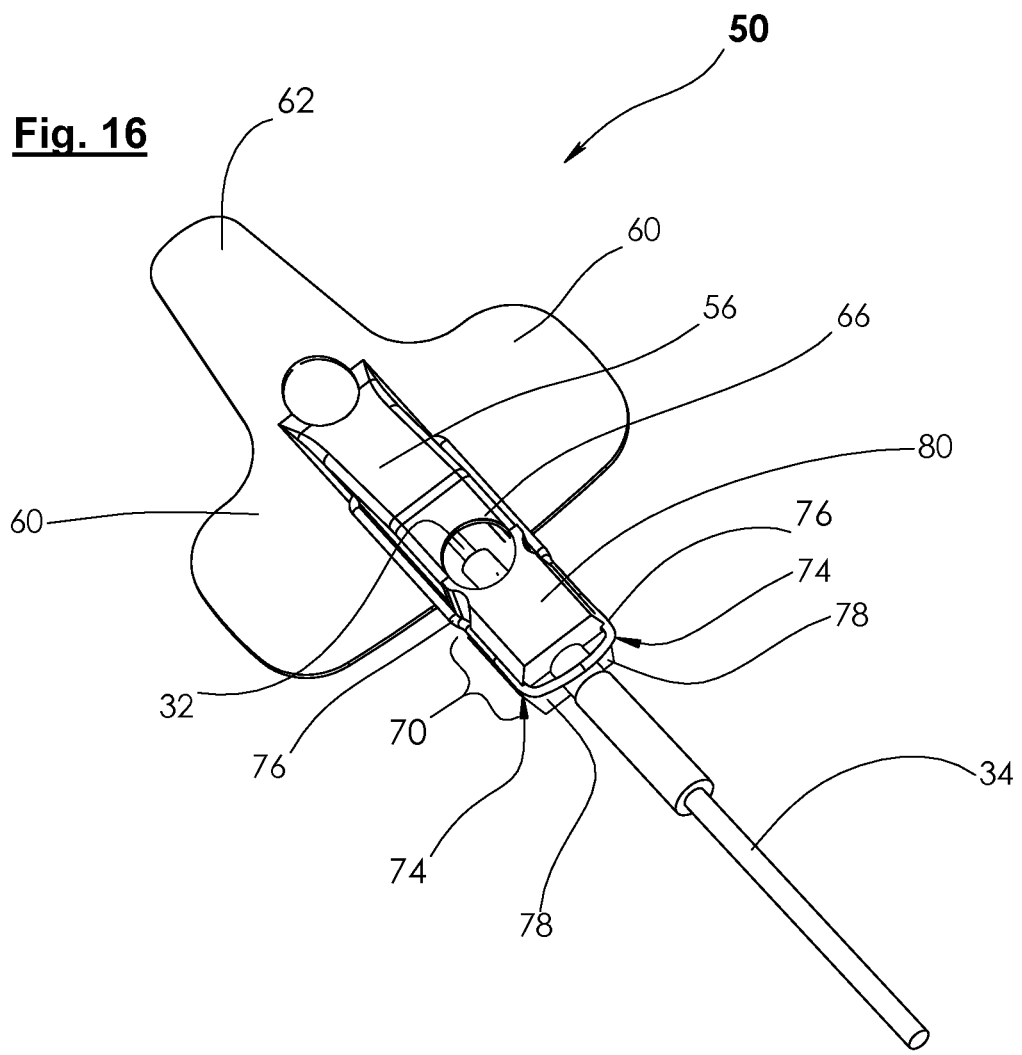

In some embodiments as shown in FIGS. 14-16, the catheter capture receptacle 70 is comprised an upper half of a "clamshell" 80 that is molded to the structural body 56 and two pieces of quarter shell 78 molded plastic that "clamshell" together around the catheter hub 30 or the catheter 32. In some embodiments, the "clamshell" action can occur because of two horizontally oriented hinges 74 molded at the junction between the catheter capture receptacle upper half shell 80 and two pieces of quarter shell 78. The hinge 74 may be a "living hinge," which is a thinned line in a molded plastic part that promotes bending or hinging at that location. The horizontally oriented hinges 74 may be "living hinges" that allow the two quarter shells 78 to swing horizontally closed from the sides as shown in FIG. 15. This allows the catheter capture receptacle 70 to close around the catheter hub 30 or the catheter 32 positively controlling the catheter hub 30, preventing its movement in any direction. The horizontal closing of the quarter shells 78 allow the capture of the catheter hub 30 without displacing the newly inserted catheter by lifting it. This is in contrast to tape and prior art anchoring devices, all of which require that the hub 30 be elevated off of the skin 4 so that the tape or anchoring device can be inserted between the hub 30 and the skin 4. This lifting movement of the hub obviously increases the probability of dislodgment of the catheter during the securing procedure.

In some embodiments, as shown in FIGS. 14-16, the previously described U-shaped piece of wire or metal maybe adapted to snap around the two quarter shells 78 to form the catheter capture receptacle lock 76. When snapped into a closed position as shown in FIG. 16, the U-shaped wire holds the two quarter shell components 78 of the catheter capture receptacle 70 in a closed and locked position. In some embodiments, the U-shaped receptacle lock 76 is adapted to also lie against the vertical sides of the structural body 56. In this location the U-shaped receptacle lock 76 provides additional longitudinal stability and strength between the skin attachment portion 52 and the catheter capture portion 54, traversing across the junction between the two portions.

In some embodiments, and as shown in FIGS. 7-9, the catheter capture receptacle 70 captures the catheter hub 30 at a slight downward angle in order to direct the catheter 32 in a straight path through the skin with a single gentle bend into the vein 8. This is in contrast to prior art devices and techniques, which attach the catheter hub to the skin and a horizontal orientation, necessitating an "S-shaped" bend in the catheter in order to penetrate the skin and vein. The "S-shaped" bend in the catheter creates an area of weakness the can preferentially kink and occlude flow.

In some embodiments, when the catheter hub 30 is captured in the catheter capture receptacle 70, the IV tubing 34 can be disconnected and changed without removing the catheter hub 30 from the catheter capture receptacle 70.

The clinician may choose a catheter that has a small horizontal wings protruding from the catheter hub 30 in order to aid with securing the catheter. In some embodiments this catheter anchoring device 50 includes small horizontal slits in the sidewalls of the two half shells 72 or quarter shells 78, that form the catheter capture receptacle 70. The horizontal slits are positioned and oriented to accommodate the wings on the catheter hub 30 that may protrude laterally out of the half shells 72 or quarter shells 78.

Figure 21:
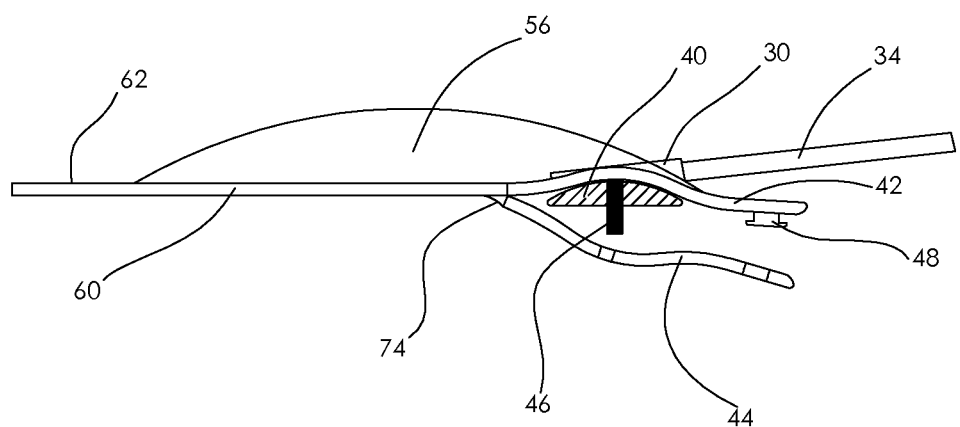
FIGS. 21-22 are side view and a top perspective view of an eighth illustrative embodiment of a catheter anchoring device.
Figure 22:
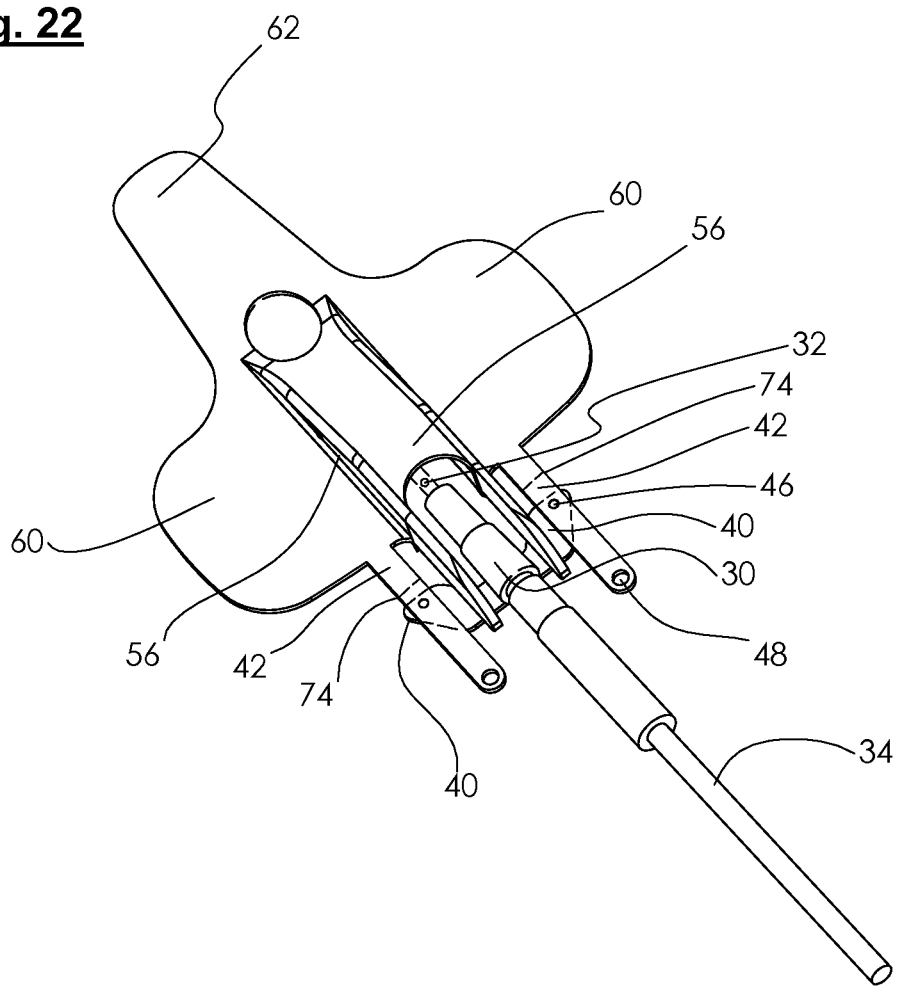

In some embodiments, other catheter capture mechanisms are anticipated. For example, as shown in FIGS. 21 and 22, there may be a horizontally oriented hinges 74 that allows horizontally oriented wing capture members 44 to snap together with two parallel base members 42. The wings 40 of a catheter hub 30 may be captured between the wing capture member 44 and the base members 42. Further security may be provided by a pin 46 that anchors the two adjacent members together and also passes through a hole in the wing 40 of the catheter hub 30. A snap 48 may also be provided to lock the wing capture member 44 in a closed position adjacent the base member(s) 42. In some embodiments additional stability may be provided by a U-shaped metal clip that captures the two adjacent members 42, 44 in the closed position, within the U-shape of the clip.

In some embodiments, the anchoring device must anchor the catheter 32 directly, rather than a catheter hub 30. For example, long venous catheters like peripherally inserted central catheters (PICC) or central venous catheters may not be advanced all of the way into the patient until the catheter hub 30 is at the skin 4. In this case, the catheter 32 itself is emerging from the skin 4 and there is no catheter hub 30 at that location to capture. Therefore the catheter anchoring device 50 must capture the catheter 32 itself.

Figure 23:
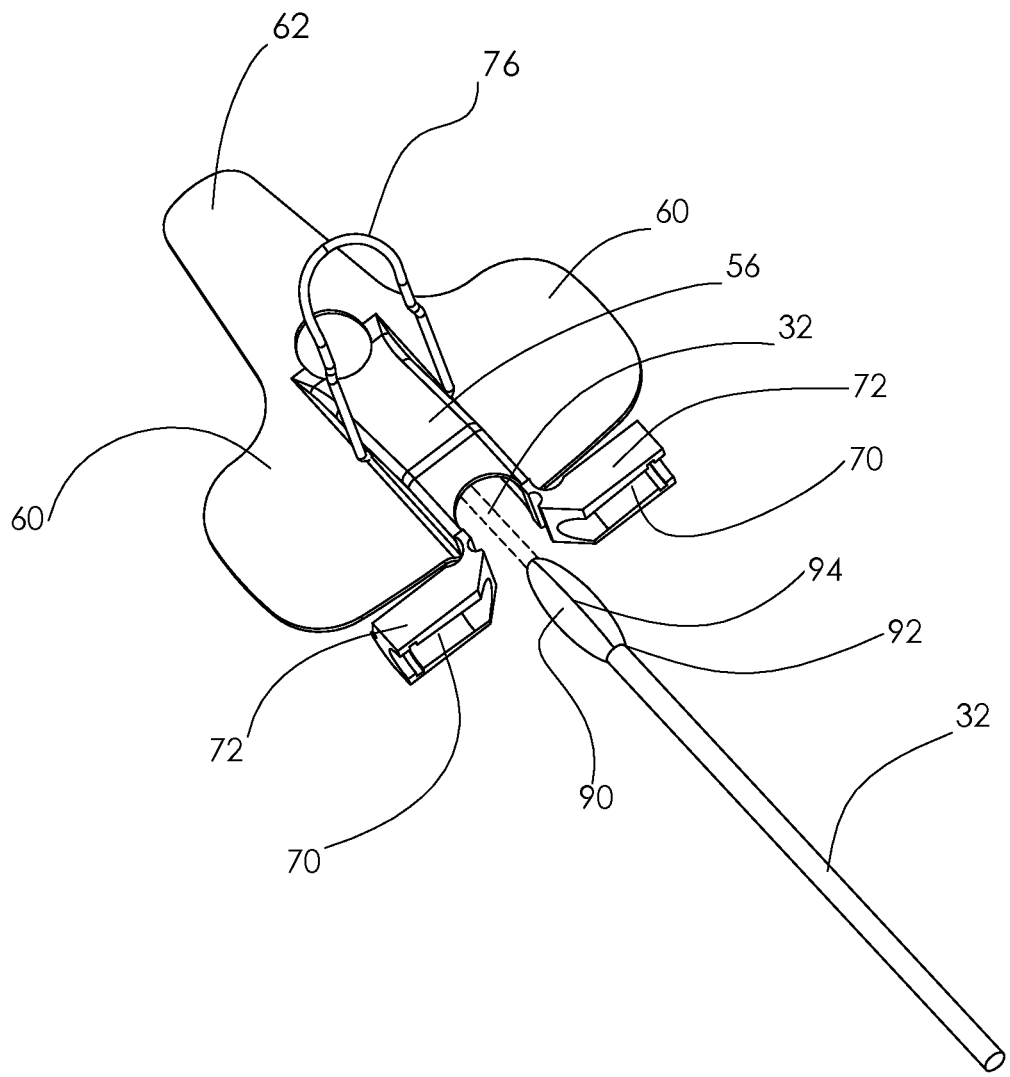
FIGS. 23-24 are top perspective views of a ninth illustrative embodiment of a catheter anchoring device with the catheter hub arranged in different positions (e.g., open, closed).
Figure 24:
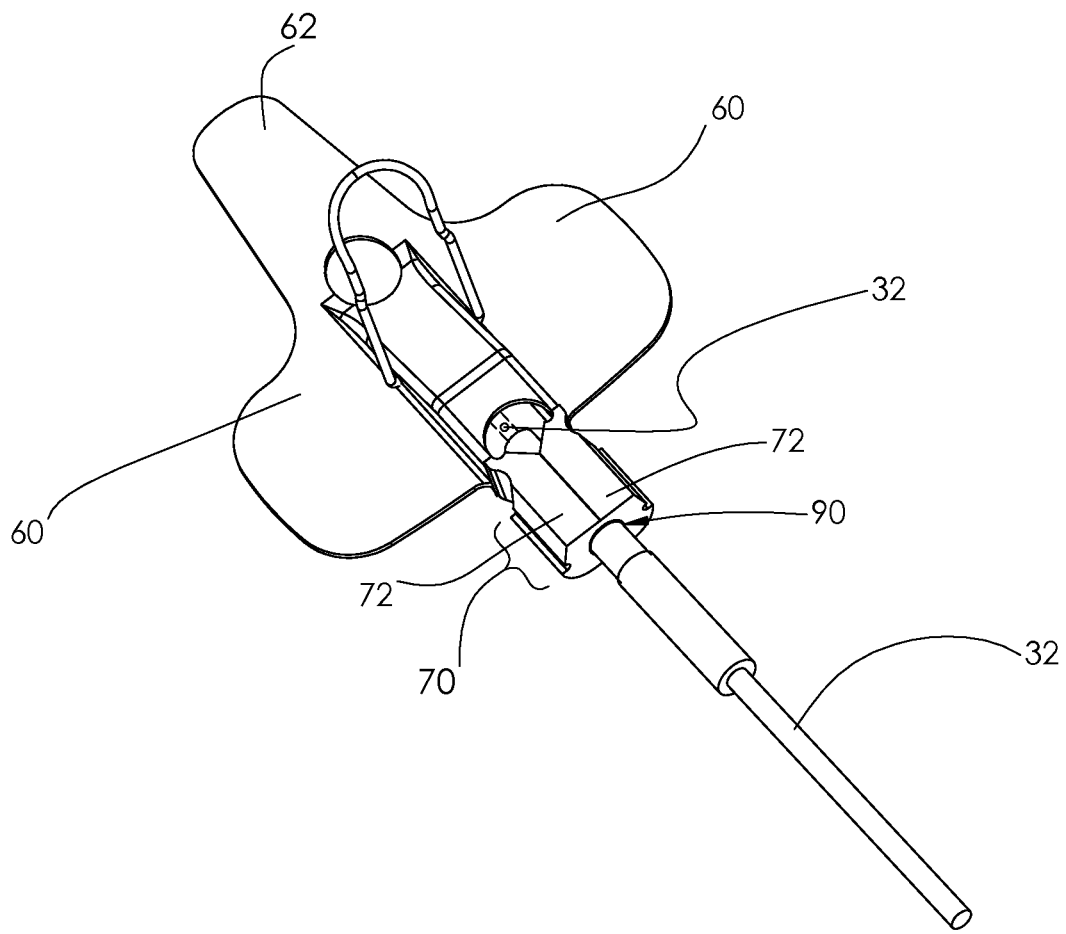

In some embodiments, the catheter anchoring device 50 is adapted to capture the catheter 32 itself. Referring to FIGS. 23 and 24, the device may include a bushing 90 that is externally sized to fit inside the catheter capture receptacle 70. In some embodiments, there is a tubular channel 92 passing through the central region of the bushing 90, to accommodate the given catheter 32 diameter. The tubular channel 92 may be slightly undersized compared to the catheter 32 diameter in order to increase the friction between the two parts. The bushing 90 may include a radial slit 94 between the external surface and the tubular channel 92, extending the full length of the channel. The radial slit 94 allows the bushing 90 to be opened for insertion of the catheter 32 into the tubular channel 92.

In some embodiments, the bushing 90 is made of a flexible, compressible material such as rubber, silicone or other polymeric substances. The flexible material of the bushing 90 allows the radial slit 94 to be spread open for introducing the catheter 32 into the tubular channel 92. The friction created between the undersized channel 92 of the bushing 90 and the catheter 32, grips the catheter 32 and prevents it from slipping through the bushing 90. Materials such as rubber, silicone, or any other suitable material further enhance the friction between the bushing 90 and the catheter 32.

As shown in FIG. 24, the bushing 90 can be placed within the half shells 72 of the catheter capture receptacle 70. In some embodiments the closure of the catheter capture receptacle 70 compresses the bushing 90, creating additional frictional force against the catheter 32, for preventing catheter slippage.

In some embodiments, the bushing 90 may be relatively inflexible and non-compressible. For example, the bushing 90 may be made of molded plastic. In some embodiments, the bushing 90 may include a clamshell design to allow opening to expose a tubular channel 92. The molded bushing 90 may include small protrusions into the tubular channel 92 that mechanically compress a portion of the catheter 32 and create mechanical friction to prevent slippage of the catheter 32. In some embodiments, the bushing 90 may be molded integrally into the catheter capture receptacle 70.

In some embodiments, the structural body includes a skin puncture site recess 66 as shown in FIG. 13, where the skin puncture site 6 is located. The skin puncture site recess 66 creates a protective housing for the skin puncture site 6 that surrounds the skin puncture site 6 without touching it. The structural body 56 of the catheter anchoring device 50 is open over the skin puncture site 6 to allow visualization of the site. This is in contrast to the prior art where the skin puncture site 6 is generally covered by an occlusive plastic film or foam. The film or foam covers and touches the skin puncture site 6 and captures the blood and serum oozing from the skin puncture site 6, creating a culture broth for growing skin bacteria at the skin puncture site 6. The protected but open design of the instant invention prevents accumulation and pooling of the blood and serum at the skin puncture site 6. It therefore also reduces the opportunity for bacteria to proliferate at the skin puncture site 6.

In some embodiments, an absorbent plug may be placed into the skin puncture site recess 66 to absorb any blood or serum oozing from the skin puncture site 6, wicking it away from the skin. The absorbent plug may be made of a fibrous material such as cotton. Alternatively the absorbent plug maybe made of other fibrous materials, absorbent foam, absorbent gel, other absorbent materials or combinations of these materials.

In some embodiments, the absorbent plug located in the skin puncture site recess 66 may include an antimicrobial material such as: silver, zinc, an antimicrobial or antibiotic. The antimicrobial agents are intended to reduce the bacterial count near the skin puncture site 6 therefore reducing the likelihood of line infections. In some embodiments, an adhesive cover made of fabric, film or paper maybe placed over the skin puncture site recess 66, to enclose the chamber created in the structural body 56, further protecting the skin puncture site 6.

In some embodiments, a small heat pack, for example utilizing an iron oxidation reaction or other chemical reaction, maybe attached to or incorporated into the catheter anchoring device 50 of the instant invention. Since catheters are introduced through the skin creating a wound and the skin is usually hypothermic, it is advantageous to warm the skin at the catheter site to normothermia (normal temperature). Normothermia or even mild hyperthermia of the skin, has been proven to activate the immune system and increase local blood flow and tissue oxygen concentration at the wound site. Activating the local immune system, increasing blood flow and oxygen concentration is advantageous in order to minimize the risk of line infection.

Normothermia or even mild hyperthermia, is also well known to promote blood flow through the vein and minimize the chance of thrombosis in the vein. Clotting of the vein (venous thrombosis) is caused by irritation to the vein by the chemicals in the IV and mechanical irritation or even denuding the wall of the vein by the catheter tip. Once the clotting process is started, thrombosis can progress to a full clot of the vein if the clot breakdown process (thrombolysis) does not occur. Both the clotting process and the clot breakdown process work better at normothermic than at hypothermic temperatures. Warming the vein with the instant invention will reduce the risk of thrombosis of the vein containing the IV.

Applying local heat to the tissue surrounding the catheter will likely increase the duration that the catheter can be left in place without complications occurring. The heat may be advantageously applied for one or more hours, one or more times daily. The objective is to periodically warm the skin and subcutaneous tissue at the catheter site to normal temperatures, but not to overheat the skin. The periodic warming of the skin allows the beneficial effects of warming to occur and yet minimizes the inconvenience and expense of the therapy.

In some embodiments, the catheter anchoring device 50 of the instant invention can be used for anchoring the access catheters and needles used in dialysis. In this instance the catheter or needle is placed into an arteriovenous (AV) shunt. These shunts are well known to have problems regarding blood flow and thrombosis. By anchoring the catheter or needle more securely with the instant invention and by providing heat as previously disclosed, complications with the arteriovenous shunts during dialysis can be minimized. Heating of the AV shunt during dialysis as well as after dialysis is anticipated in this invention.

As shown in FIGS. 5 and 6, the skin attachment portion 52 of the catheter anchoring device 50 of the instant invention is primarily attached to the skin overlaying and lateral to the subcutaneous catheter 38. To meet this requirement, the device must transmit; pulling, pushing, twisting or lateral forces applied to the hub or the IV line, primarily to the skin overlying and lateral to the subcutaneously located catheter 32 (e.g., at 38).

Many of the prior art catheter anchoring devices include a tape or plastic film with adhesive, which extends from the catheter hub 30. While pulling forces maybe transmitted by this design, these prior art devices do not qualify as the instant invention because there is no structural body 56 that can transmit pushing, twisting and lateral forces from the catheter hub 30, to the skin overlying the catheter 32 (e.g., at 38). The instant invention requires that the pushing, pulling, twisting and lateral forces applied to the catheter hub 30 are all transmitted to the skin overlying and lateral to the subcutaneous catheter 32 (e.g., 38), not primarily at 36.

Ascertaining that the catheter anchoring device 50 is primarily attached to the skin overlying the catheter is simple if there is no attachment or minimal attachment to the skin adjacent to catheter hub 36. This is one preferred embodiment of this invention.

Ascertaining that the catheter anchoring device 50 is primarily attached to the skin overlying the catheter 38 maybe confusing if there is significant adhesive attachment to the skin on both sides of the skin puncture site 6, over the catheter 38 and adjacent the hub (e.g., at 36). In this case, three functional tests may be helpful for differentiating the primary attachment site. First, push the catheter hub 30 into the skin 4. If the skin overlaying the subcutaneous catheter 38 moves in the same direction as the pushing movement, the device is attached at that location and includes a structural body 56 that is stiff enough to transmit the pushing force. This combination is essential for the primary attachment over the subcutaneous catheter 38 to be created.

Figure 25:
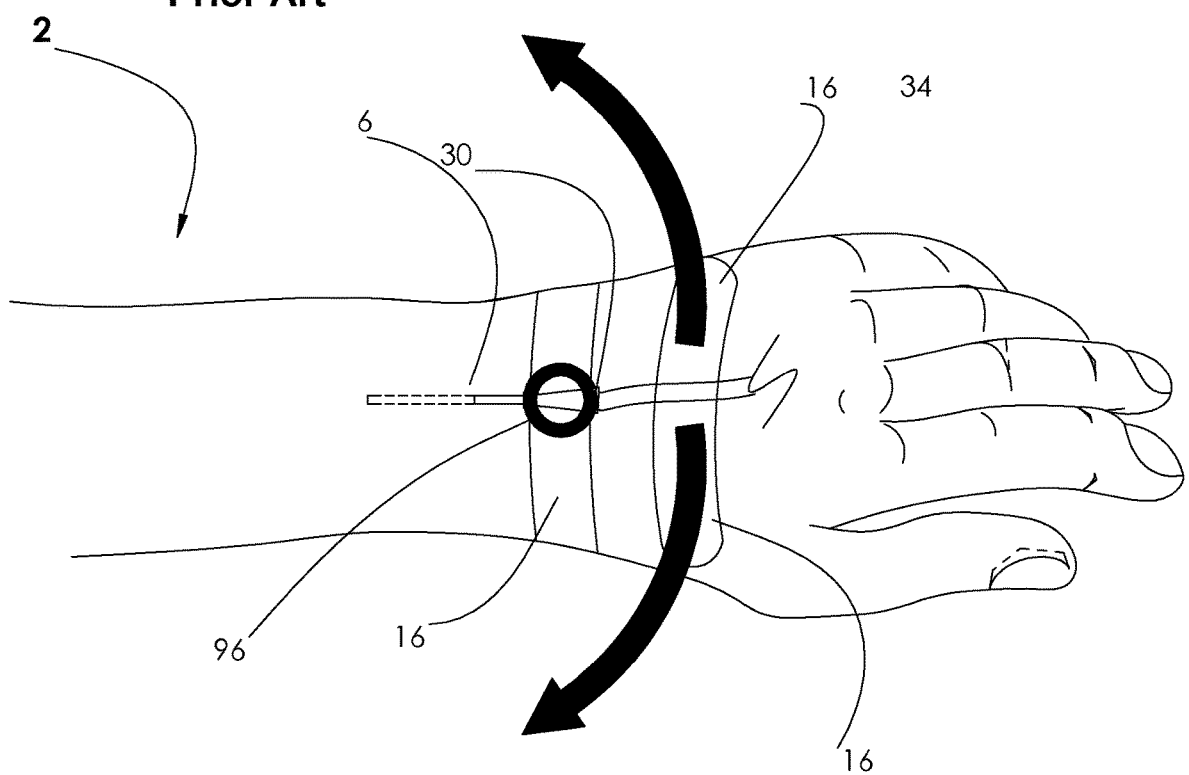
FIG. 25 is a top view illustration of the prior art depicting an axis of rotation.
Figure 26:
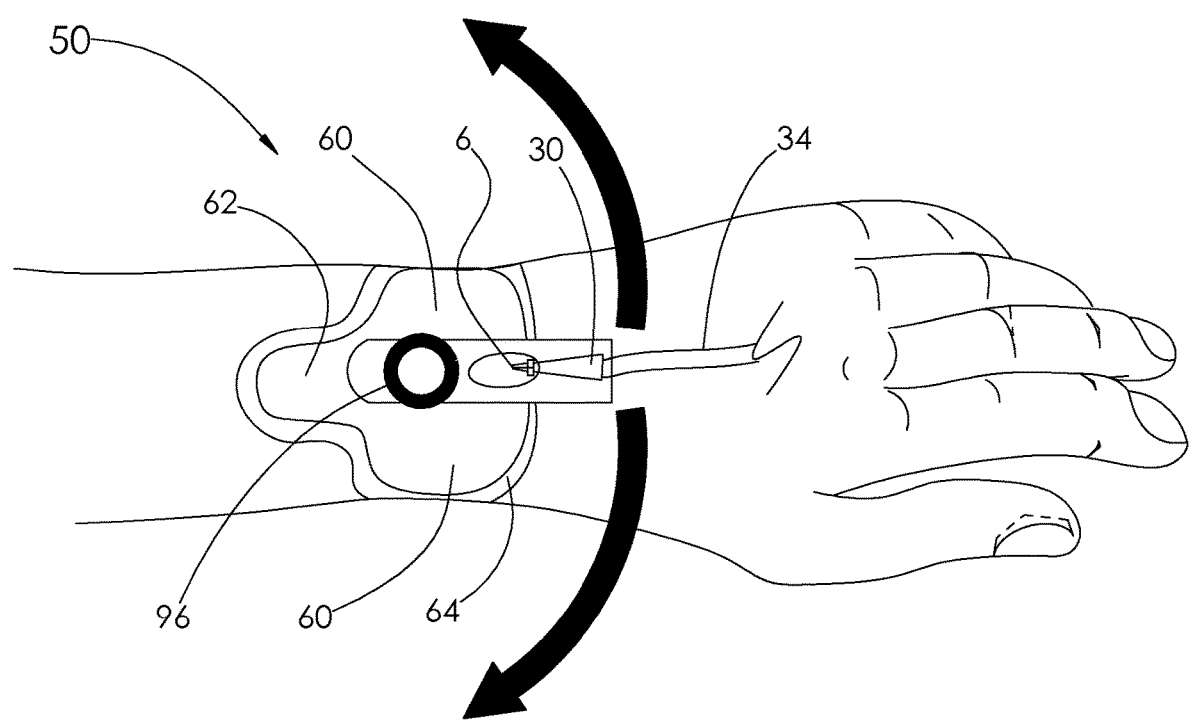
FIG. 26 is a top view illustration of embodiments described herein depicting an axis of rotation.

Second, twist the catheter hub 30 around a vertical twisting axis 96 and observe where the vertical twisting access 96 is located (e.g., axis of rotation). If the twisting motion occurs at the catheter hub 30, the primary attachment site is adjacent to hub (e.g., at 36). If the twisting axis 96 is over the subcutaneously located catheter 38 and the twisting motion creates a lever action with the catheter hub 30 at the end of the lever, the primary attachment site is over the catheter 38. For example, see axis of rotation that passes into the page at 96 in FIGS. 25-26. Finally, if a lateral movement of the catheter hub 30 results in significant lateral movement of the skin over the subcutaneous catheter 38, the primary attachment site is over the catheter 38.

In some embodiments, a minor attachment or loose attachment between the catheter hub 30 and the adjacent skin (e.g., at 36) may be added to this invention without violating the primary attachment being the skin overlaying and adjacent to catheter 38.

In the forgoing detailed description, the invention has been described with reference to specific embodiments. However, it may be appreciated the various modifications, combinations of embodiments, and changes can be made without departing from the scope of the invention as set forth in the appended claims.

Various examples have been described. These and other examples are within the scope of the following claims.

What is claimed is:

1. A catheter anchoring device for securing a percutaneous medical catheter inserted at a skin puncture site to a skin of a body such that the catheter is subcutaneous when anchored to the patient's skin by the catheter anchoring device, the catheter being elongate and defining opposite sides along the elongation of the catheter, the catheter anchoring device comprising:
    a catheter capture portion configured to engage with a portion of the catheter; and
    a skin attachment portion coupled to the catheter capture portion, the skin attachment portion configured to adhesively attach the anchoring device to the skin,
    the skin attachment portion comprises an adhesive surface configured to adhesively attach the anchoring device to the skin, wherein more than 50% of the adhesive surface of the skin attachment portion extends beyond the catheter capture portion in a direction along the elongation of the catheter, and being positioned on opposite sides along the elongation of the catheter.

2. The catheter anchoring device of claim 1, wherein the catheter capture portion is loosely attached to the skin adjacent the catheter capture portion.

3. The catheter anchoring device of claim 1, wherein the catheter capture portion is not attached to the skin adjacent the catheter capture portion.

4. The catheter anchoring device of claim 1, wherein the catheter capture portion comprises an end portion, and wherein when the catheter anchoring device is secured to the body, a twisting force applied to the end portion results in a twisting motion about an axis of rotation substantially central to the skin overlaying and lateral to the subcutaneously located catheter.

5. The catheter anchoring device of claim 1, wherein the skin puncture site is not covered with polymeric film, foam or other occlusive materials.

6. The catheter anchoring device of claim 1, wherein the skin attachment portion comprises a structural body that surrounds and protects the skin puncture site without touching the skin puncture site.

7. The catheter anchoring device of claim 1, wherein the catheter capture portion comprises a catheter hub, and wherein a longitudinal movement of the catheter capture portion in either direction results in a movement of the skin overlaying and lateral to the subcutaneously located catheter in the same direction and distance as the movement of the catheter hub and catheter.

8. The catheter anchoring device of claim 1, wherein the catheter capture portion comprises two half-shell parts that swing together in horizontal arcs, pivoting on two vertically oriented hinges positioned between the half-shells and the structural body of the skin attachment portion, and wherein the two half-shell parts swing together in horizontal arcs to create a catheter capture receptacle configured to capture the catheter or a catheter hub within and between the half-shell parts.

9. The catheter anchoring device of claim 8, wherein a U-shaped receptacle lock that hinges horizontally from the structural body of the skin attachment portion, traverses the hinges of the half-shells and captures the two half-shell parts within the U-shaped receptacle lock, to lock the catheter capture receptacle in the closed position around the catheter or the catheter hub.

10. The catheter anchoring device of claim 1, wherein the catheter capture portion comprises one half-shell part attached to the structural body of the catheter anchoring device and two quarter-shell parts that swing together in vertical arcs, pivoting on two horizontally oriented hinges positioned between the half-shell and two quarter-shell parts, wherein the two quarter-shell parts swing together in vertical arcs to create a catheter capture receptacle for capturing the catheter or catheter hub within and between the half-shell part and the two quarter-shell parts.

11. The catheter anchoring device of claim 10, wherein a U-shaped receptacle lock hinges horizontally from the structural body of the skin attachment portion to capture the two quarter-shell parts within the U-shape to lock the catheter capture receptacle in the closed position around the catheter or catheter hub.

12. The catheter anchoring device of claim 1, wherein the skin attachment portion is attached to the skin overlaying a distal tip of the catheter when the catheter is located subcutaneously.

13. A catheter anchoring device for securing a percutaneous medical catheter inserted at a skin puncture site to a skin of a body such that the catheter is subcutaneous when anchored to the patient's skin by the catheter anchoring device, the catheter being elongate and terminating in a distal tip, the catheter anchoring device comprising:
    a catheter capture portion configured to engage a portion of the catheter; and
    a skin attachment portion coupled to the catheter capture portion, the skin attachment portion configured to adhesively attach the catheter anchoring device to the skin,
    the skin attachment portion comprises an adhesive surface configured to adhesively attach the anchoring device to the skin, wherein more than 50% of the adhesive surface of the skin attachment portion extends beyond the catheter capture portion in a direction along the elongation of the catheter, so as to permit a longitudinal movement of the catheter capture portion when the catheter is anchored to the patient's skin, thereby permitting an equal movement of the skin overlaying the catheter in either direction.

14. The catheter anchoring device of claim 13, wherein the skin puncture site is not covered with polymeric film, foam or other occlusive materials.

15. The catheter anchoring device of claim 13, wherein the skin attachment portion includes a structural body that surrounds and protects the skin puncture site without touching the skin puncture site.

16. The catheter anchoring device of claim 13, wherein the skin attachment portion is primarily attached to the skin overlaying and lateral to the subcutaneously located catheter.

17. The catheter anchoring device of claim 13, wherein the skin attachment portion comprises an adhesive surface configured to adhesively attach the anchoring device to the skin, wherein more than 50% of the adhesive surface of the skin attachment portion is configured to be attached to the skin overlaying and lateral to the subcutaneously located catheter.

18. The catheter anchoring device of claim 13, wherein the catheter capture portion comprises an end portion, and wherein when the catheter anchoring device is secured to the body, a twisting force applied to the end portion results in a twisting motion about an axis of rotation substantially central to the skin overlaying and lateral to the subcutaneously located catheter.

19. The catheter anchoring device of claim 13, wherein the catheter capture portion comprises two half-shell parts that swing together in horizontal arcs, pivoting on two vertically oriented hinges positioned between the half-shells and the structural body of the skin attachment portion, and wherein the two half-shell parts swing together in horizontal arcs to create a catheter capture receptacle configured to capture the catheter or a catheter hub within and between the half-shell parts.

20. The catheter anchoring device of claim 13, wherein the catheter capture portion comprises one half-shell part attached to the structural body of the catheter anchoring device and two quarter-shell parts that swing together in vertical arcs, pivoting on two horizontally oriented hinges positioned between the half-shell and two quarter-shell parts, wherein the two quarter-shell parts swing together in vertical arcs to create a catheter capture receptacle for capturing the catheter or catheter hub within and between the half-shell part and the two quarter-shell parts.

21. A catheter anchoring device for securing a percutaneous medical catheter inserted at a skin puncture site to a skin of a body, the catheter anchoring device comprising:
a catheter capture portion configured to engage a portion of the catheter protruding from the skin after percutaneous placement of the catheter into the body;
a skin attachment portion configured to adhesively attach the catheter anchoring device to the skin, wherein an entirety of the skin attachment portion extends beyond the catheter capture portion in a direction along the elongation of the catheter.

22. The catheter anchoring device of claim 21, wherein the skin attachment portion is primarily attached to the skin overlaying and lateral to the subcutaneously located catheter.

23. The catheter anchoring device of claim 21, wherein the skin attachment portion comprises an adhesive surface configured to adhesively attach the anchoring device to the skin, wherein more than 50% of the adhesive surface of the skin attachment portion is configured to be attached to the skin overlaying and lateral to the subcutaneously located catheter.

24. The catheter anchoring device of claim 21, wherein the catheter capture portion comprises an end portion, and wherein when the catheter anchoring device is secured to the body, a twisting force applied to the end portion results in a twisting motion about an axis of rotation substantially central to the skin overlaying and lateral to the subcutaneously located catheter.

\* \* \* \* \*